(12) United States Patent
Balasubramanian et al.

(10) Patent No.: US 12,728,193 B2
(45) Date of Patent: Sep. 8, 2026

(54) MEDICAL DELIVERY ASSEMBLY WITH MULTI-PORT NEEDLE

(71) Applicant: Bard Peripheral Vascular, Inc., Franklin Lakes, NJ (US)

(72) Inventors: Sivaramakrishnan Balasubramanian, Cary, NC (US); Christopher Anthony Basciano, Apex, NC (US); Christopher Dean Drobnik, Wauconda, IL (US); Casey Tyler Hebert, Loveland, CO (US); Brandon David Simmons, Tempe, AZ (US); Nathan Spangenberg, Cary, NC (US); Amanda Thystrup, Phoenix, AZ (US); Mark Nicholas Wright, Coventry, RI (US)

(73) Assignee: Bard Peripheral Vascular, Inc.

( * ) Notice: Subject to any disclaimer, the term of this patent is extended or adjusted under 35 U.S.C. 154(b) by 837 days.

(21) Appl. No.: 18/003,058

(22) PCT Filed: Jun. 25, 2020

(86) PCT No.: PCT/US2020/039591

§ 371 (c)(1),
(2) Date: Dec. 22, 2022

(87) PCT Pub. No.: WO2021/262174

PCT Pub. Date: Dec. 30, 2021

(65) Prior Publication Data

US 2023/0248899 A1 Aug. 10, 2023

(51) Int. Cl.
*A61M 5/00* (2006.01)
*A61M 5/158* (2006.01)

(52) U.S. Cl.
CPC ............ *A61M 5/007* (2013.01); *A61M 5/158* (2013.01); *A61M 2205/3331* (2013.01)

(58) Field of Classification Search
CPC ...... A61M 5/1409; A61M 5/14; A61M 5/142; A61M 5/14216; A61M 5/1456;
(Continued)

(56) References Cited

U.S. PATENT DOCUMENTS 1,615,873 A * 2/1927 Fitch .................... A61M 5/162 604/411
2,911,123 A * 11/1959 Saccomanno ......... A61M 5/162 220/521

(Continued)

FOREIGN PATENT DOCUMENTS

CN 2557149 Y 6/2003
CN 204133900 Y 2/2015

(Continued)

OTHER PUBLICATIONS

Chinese Office Action for Appln. No. 202080104476.3 mailed Jun. 5, 2024, 10 pages.

(Continued)

*Primary Examiner* — Cris L. Rodriguez
(74) *Attorney, Agent, or Firm* — Dinsmore & Shohl LLP

(57) ABSTRACT

A delivery assembly includes a console including a vial containment region and a vial engagement mechanism extending from the console within the vial containment region. The engagement mechanism is configured to engage a vial assembly including a particulate material. The delivery assembly further includes a multi-port needle with a top distal port and bottom proximal port(s), the needle configured to puncture a septum of the vial assembly when the vial assembly is in the locked position, in which the top distal port is at a distance above the particulate material in the vial assembly. The ports are configured to inject a fluid into the vial assembly to mix with the particulate material upon actuation of the vial engagement mechanism in a first direction and to receive a resulting mixed fluid from the vial (Continued)

assembly upon actuation of the vial engagement mechanism in a second opposite direction.

18 Claims, 14 Drawing Sheets

(58) Field of Classification Search
CPC .......... A61M 5/14566; A61M 5/16809; A61M 5/172; A61M 5/178; A61M 5/204; A61M 5/2448; A61M 25/003; A61M 2005/1787; A61M 2005/2414; A61M 2005/247; A61M 5/1408; A61M 5/1582; A61M 5/007; A61M 5/158
USPC .......................................... 600/4, 5, 411–412
See application file for complete search history.

(56) References Cited

U.S. PATENT DOCUMENTS 3,552,441 A * 1/1971 Luhleich ............... F16K 11/065 138/155
3,810,469 A * 5/1974 Hurschman ........... A61M 5/284 604/196
4,373,559 A * 2/1983 Mowles ................ A61J 1/2089 141/98
4,507,113 A * 3/1985 Dunlap ................... A61M 5/30 604/71
4,714,098 A * 12/1987 Stuckel .................. A63B 41/12 141/85
4,874,366 A * 10/1989 Zdeb ................... A61M 5/1409 604/518
4,976,894 A * 12/1990 Robinson ............ B01F 23/2361 141/330
5,049,129 A * 9/1991 Zdeb ................... A61M 5/1409 604/413
5,226,900 A * 7/1993 Bancsi ................ A61M 5/1409 604/905
5,364,387 A * 11/1994 Sweeney ............... A61J 1/2096 604/239
5,397,303 A * 3/1995 Sancoff ................. A61J 1/1425 604/82
5,423,753 A * 6/1995 Fowles ............... A61M 5/1409 604/87
5,478,328 A 12/1995 Silverman et al.
5,699,838 A * 12/1997 Catallo ................. B29C 70/443 264/269
5,800,407 A 9/1998 Eldor
5,868,721 A * 2/1999 Marinacci ............... A61M 5/24 604/413
6,261,272 B1 7/2001 Gross et al.
6,280,424 B1 8/2001 Chang et al.
6,689,108 B2 * 2/2004 Lavi ........................ A61M 5/19 604/246
7,402,155 B2 7/2008 Palasis et al.
7,736,353 B2 * 6/2010 Reynolds .............. A61J 1/2096 604/414
8,540,686 B2 * 9/2013 Steube .................. A61J 1/2096 604/272
8,720,501 B2 * 5/2014 Thilly ..................... B65B 3/003 141/59
9,393,364 B2 7/2016 Fischer, Jr.
9,629,987 B2 4/2017 Anand et al.
9,694,166 B2 7/2017 Hurt
10,456,815 B1 10/2019 Palmaz
2002/0004643 A1 * 1/2002 Carmel ............... A61M 5/2448 604/82
2004/0092893 A1 5/2004 Haider et al.
2005/0031676 A1 2/2005 Wong et al.
2005/0081953 A1 * 4/2005 Yui ...................... B67D 3/0032 141/349
2005/0277906 A1 * 12/2005 Brugger ................ A61M 5/162 604/411
2007/0219460 A1 9/2007 Goldenberg
2008/0172012 A1 7/2008 Hiniduma-Lokuge et al.
2010/0010413 A1 * 1/2010 Loiterman .......... A61M 5/3291 604/266
2010/0063460 A1 * 3/2010 Reed ..................... A61M 5/162 604/272
2010/0108062 A1 5/2010 Ganem et al.
2010/0217231 A1 8/2010 Ilan et al.
2010/0330589 A1 * 12/2010 Bahrami ................. A61P 35/00 435/7.9
2011/0009807 A1 * 1/2011 Kjeken .................. A61N 1/327 604/501
2012/0192976 A1 * 8/2012 Rahimy ................ A61J 1/2089 137/798
2013/0253448 A1 9/2013 Baron et al.
2014/0014210 A1 1/2014 Cederschild
2015/0051583 A1 * 2/2015 Horvath ............ A61M 25/0015 604/508
2018/0207356 A1 7/2018 Joseph et al.
2019/0184097 A1 6/2019 Sweeney et al.
2019/0374716 A1 * 12/2019 Diaz .................. A61M 5/31511
2020/0276085 A1 * 9/2020 Linkner ............. A61K 38/4893
2024/0115801 A1 * 4/2024 Diaz ....................... A61M 5/19

FOREIGN PATENT DOCUMENTS

JP 2014506494 A 3/2014
JP 2015503422 A 2/2015
WO WO 8503433 A * 8/1985 ................ A61J 1/00
WO WO-0029049 A1 * 5/2000 .......... A61M 5/2448
WO WO-02083228 A2 * 10/2002 ............ A61M 5/158
WO 2009060419 A2 5/2009
WO 2013103864 A1 7/2013
WO 2013134505 A1 9/2013
WO 2019222713 A1 11/2019

OTHER PUBLICATIONS

International Search Report and Written Opinion dated Feb. 9, 2021, in International Application No. PCT/US2020/039591.
Japanese Office Action dated Jan. 26, 2024 pertaining to Japanese application No. 2022-580325 filed Dec. 26, 2022, pp. 1-11.

* cited by examiner 580
581
582
583
584
585
586
586A
587
588
589
590
592
4
4
4
4

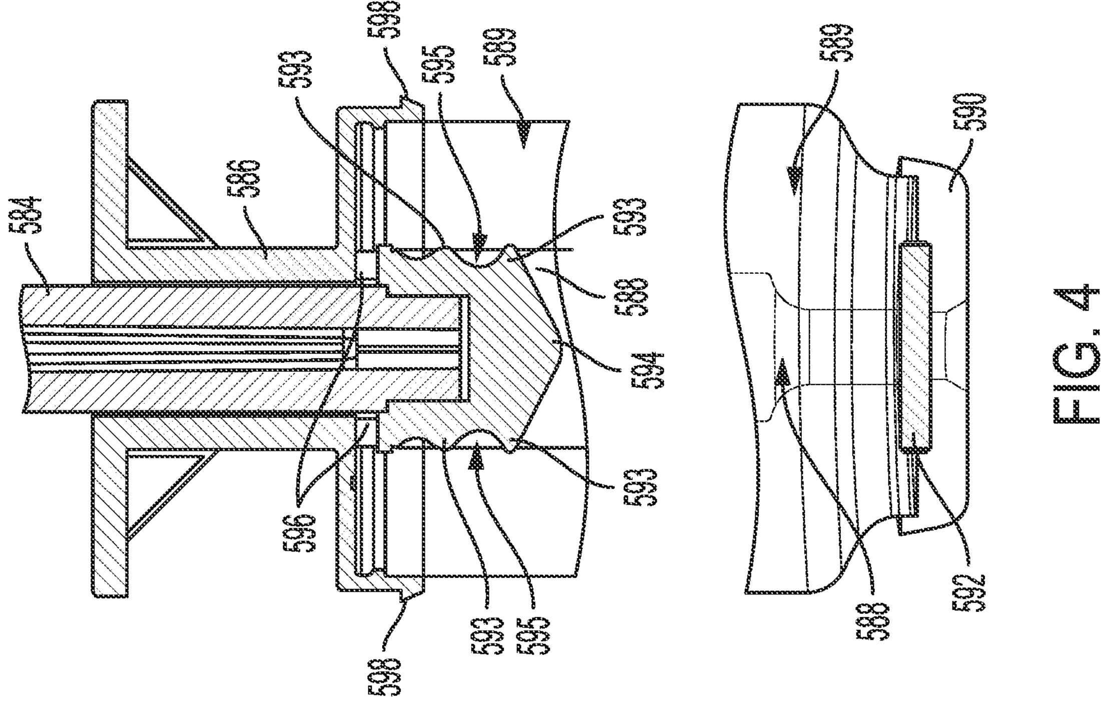
FIG. 4
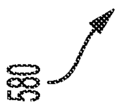

MEDICAL DELIVERY ASSEMBLY WITH MULTI-PORT NEEDLE

CROSS-REFERENCE TO RELATED APPLICATIONS

This application is a U.S. National Phase of International Application No. PCT/US2020/039591, entitled "Medical Delivery Assembly With Multi-Port Needle" and filed Jun. 25, 2020, which is incorporated herein by reference in its entirety.

TECHNICAL FIELD

The present disclosure generally relates to components of medical devices for treating cancer, and more particularly to needle components of medical devices configured and operable to deliver radioactive compounds to a treatment area within a patient's body in procedures such as transarterial radioembolization.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial Radioembolization is a transcatheter intra-arterial procedure performed by interventional radiology and is commonly employed for the treatment of malignant tumors. During this medical procedure, a microcatheter is navigated into a patient's liver where radioembolizing microspheres loaded with a radioactive compound, such as yttrium-90 ($^{90}Y$), are delivered to the targeted tumors. The microspheres embolize blood vessels that supply the tumors while also delivering radiation to kill tumor cells.

Generally, needle components of syringes for manually administering the radioactive compound are prone to inconsistent flow rates and pressures and clogging. Such clogging may require cleaning of the needle components and/or connected components, which may cause insufficient injection rates and/or less efficient delivery resulting in decreased bead dispersion. Such decreased bead dispersion may impact efficacy of the treatment.

Accordingly, a need exists for needled components of a medical device that is configured and operable to perform radioembolization that incorporates a simplistic design and consistent means for administering constant flow rates and pressure of the radioactive compound to the patient's body while preventing or reducing clogging during such delivery.

SUMMARY

In accordance with an embodiment of the disclosure, a particulate material delivery assembly may include a console including a vial containment region, a vial assembly comprising a particulate material, a vial engagement mechanism extending from the console within the vial containment region, wherein the vial engagement mechanism is configured to engage the vial assembly and move the vial assembly to a locked position, and a multi-port needle configured to puncture a septum of the vial assembly when the vial assembly is in the locked position. The multi-port needle may include a top distal port of a first diameter and at least a bottom proximal port of a second diameter that is smaller than the first diameter, the top distal port and the at least the bottom proximal port configured to inject a fluid into the vial assembly to mix with the particulate material upon actuation of the vial engagement mechanism in a first direction and to receive a resulting mixed fluid from the vial assembly upon actuation of the vial engagement mechanism in a second direction opposite the first direction. The top distal port may be further configured to be at a distance above and spaced away from the particulate material in the vial assembly when in the locked position.

In another embodiment, a method of use of a particulate material delivery assembly to deliver particulate may include engaging a vial engagement mechanism extending from a console within a vial containment region of the console with a vial assembly comprising a particulate material, moving the vial assembly engaged with the vial engagement mechanism to a locked position, and puncturing a septum of the vial assembly with a multi-port needle when the vial assembly is in the locked position. The multi-port needle may include a top distal port of a first diameter and at least a bottom proximal port of a second diameter that is smaller than the first diameter, and the top distal port is further configured to be at a distance above and spaced away from the particulate material in the vial assembly when in the locked position. The method may further include injecting through the top distal port and the at least the bottom proximal port a fluid into the vial assembly to mix with the particulate material to generate a resulting mixed fluid in the vial assembly upon actuation of the vial engagement mechanism in a first direction, and receiving through top distal port and the at least the bottom proximal port the resulting mixed fluid from the vial assembly into the multi-port needle upon actuation of the vial engagement mechanism in a second direction opposite the first direction.

These and additional features provided by the embodiments described herein will be more fully understood in view of the following detailed description, in conjunction with the drawings.

BRIEF DESCRIPTION OF THE DRAWINGS

FIG. 4 is a partial cross-sectional view of the vial assembly of FIG. 4, the cross-section taken along line 4-4 of FIG. 3;

DETAILED DESCRIPTION

Figure 1:
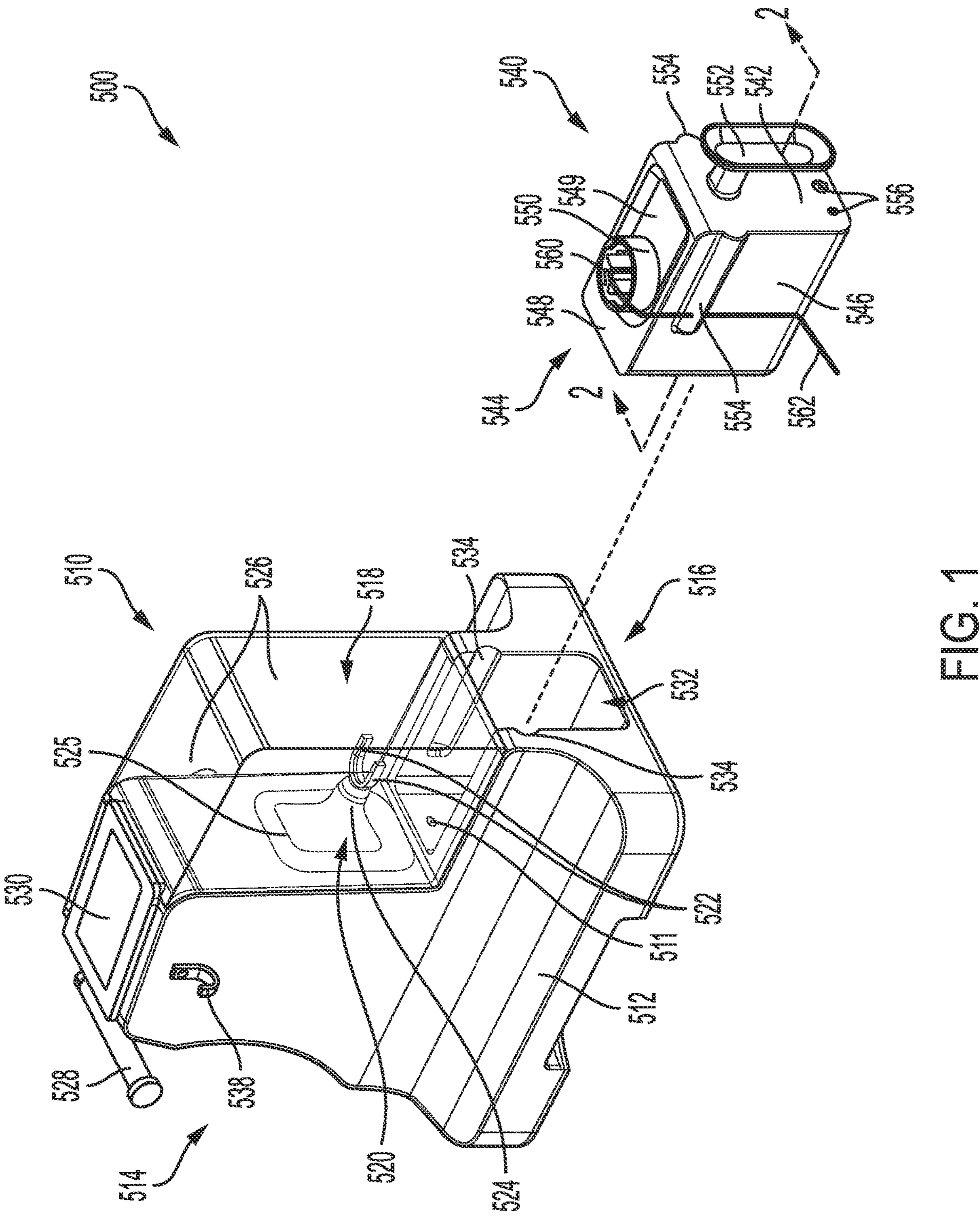
FIG. 1 is a perspective view of a delivery device including a protective shield and a vial sled according to one or more embodiments shown and described herein.

Reference will now be made in detail to various embodiments of delivery devices for administering radioactive compounds to a patient, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Unless otherwise defined, all technical and scientific terms used herein have the same meaning as commonly understood by one of ordinary skill in the art to which the disclosure belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal," "vertical," "distal" and "proximal" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present disclosure and the embodiments thereof to be described herein may be used in any desired orientation. Moreover, horizontal and vertical walls need generally only be intersecting walls, and need not be perpendicular. As used herein, the singular forms "a," "an" and "the" include plural referents unless the context clearly dictates otherwise. Thus, for example, reference to "a" component includes aspects having two or more such components, unless the context clearly indicates otherwise.

In embodiments described herein, a particulate material delivery assembly may include a radioembolization delivery device. A radioembolization delivery device comprises a medical device configured to deliver radioactive compounds to a treatment area within a patient's body in procedures such as transarterial radioembolization. The radioactive compounds may be a mixed solution of saline and radioactive microspheres (i.e., a particulate) mixed in a vial of a vial assembly. The needle may include one or more ports as an outlet to inject fluid (i.e., saline), such as from a syringe or catheter line, into a vial including the radioactive microspheres to generate the mixed solution and as an inlet to deliver the mixed solution to the patient.

At least two ports of a multi-port needle in embodiments may each include a respective diameter and disposition on the needle to optimize homogenous mixing of the mixed solution and prevent or reduce needle port clogging. For example, when an embolization procedure is performed using microspheres, the particles in the mixed fluid solution (i.e., mixed with saline) are injected to the vasculature via a catheter coupled to the needle. If the bolus of particles is too large, either due to less homogenous mixing or settling due to gravity, the particles in the mixed solution can clog the microcatheter thereby preventing administration. The physician can then try to restore flow through the catheter by breaking up the bolus. If this is not successful, then the physical may have to restart the procedure with a fresh catheter. Both solutions may increase the procedure time and cost while not preventing the risk of another clog occurring.

The multi-port needle as described herein, and in greater detail further below, includes anti-clogging features via the at least two ports to prevent or reduce such potential clogging while being configured to optimize mixing. The multi-port needle may include an upper top distal port and one or more lower bottom proximal ports having smaller diameters than the upper top distal port to collectively create a high velocity fluid jet stream. The lower bottom proximal ports can evenly spaced around a circumference of the needle. The upper top distal port for clog prevention may be a slightly larger port that is a set distance from the lower bottom proximal ports and is configured to be disposed above a settled particulate material in a vial when injected into the vial. A ratio of the area of the ports to the needle inner lumen and rest of the fluid path may assist to determine the number and spacing of the lower ports to optimize velocity output.

I. Mechanical Delivery Device with Removable Sled Assembly

FIGS. 1-10 show an embodiment of a delivery device 500 that is configured and operable to deliver a radioactive material (e.g., radioembolizing beads) while reducing radioactive emissions during use of the delivery device 500. The delivery device 500 may operate as described in International PCT App. No. PCT/2019/033001, filed May 17, 2019, the entirety of which is incorporated herein, except with respect to a multi-port needle 559 utilized with the delivery device 500 and as described in greater detail below with respect to FIGS. 11-14 and in one or more embodiments herein.

Referring initially to FIG. 1, the delivery device 500 comprises a console assembly 510, which includes a console. The delivery device 500 may include a sled assembly 540 that is operable to transition between a coupled state and decoupled state relative to the console assembly 510. The console assembly 510 of the delivery device 500 comprises a base 512 defined by and extending between a proximal end 514 and a distal end 516. The proximal end 514 of the base 512 includes a handle (delivery handle) 528 movably coupled to the console assembly 510 and an interface display 530 positioned on the console assembly 510.

The proximal end 514 of the base 512 further includes an attachment device 538 that is configured to securely retain an external device to the base 512 of the console assembly 510. The attachment device 538 is operable to facilitate an attachment of a complimentary device to the console assembly 510 for use with the delivery device 500 during a procedure.

Still referring to FIG. 1, the distal end 516 of the console assembly 510 defines a vial containment region 518 that is sized and shaped to receive the console assembly 510 therein, as will be described in greater detail herein. The console assembly 510 further includes a vial engagement mechanism 520 extending from the base 512 adjacent to the distal end 516. In particular, the vial engagement mechanism 520 extends laterally outward from the base 512 of the console assembly 510 toward the distal end 516. The vial engagement mechanism 520 is positioned within the vial containment region 518 of the console assembly 510 and is movably coupled to the handle 528. In particular, the handle 528 of the console assembly 510 is operable to move, and in particular translate, the vial engagement mechanism 520 within the vial containment region 518 in response to an actuation of the handle 528.

The console assembly 510 includes a mechanical assembly disposed within the base 512 that is configured and operable to convert a manual motion of the handle 528 to a corresponding linear displacement of the vial engagement mechanism 520. In the present example, the mechanical assembly is coupled to the handle 528 and the vial engagement mechanism 520 such that selective actuation of the handle 528 at the proximal end 514 causes a simultaneous actuation of the vial engagement mechanism 520 at the distal end 516.

The sled cavity 532 is sized and shaped to receive the sled assembly 540 therein. As will be described in greater detail herein, the sled assembly 540 is configured to store and administer therapeutic particles (e.g., radioactive beads, microspheres, medium) therethrough. In particular, the sled assembly 540 is configured to partially receive a vial assembly 580 therein for administering the therapeutic particles from the delivery device 500 and to a patient during a procedure.

Figure 2:
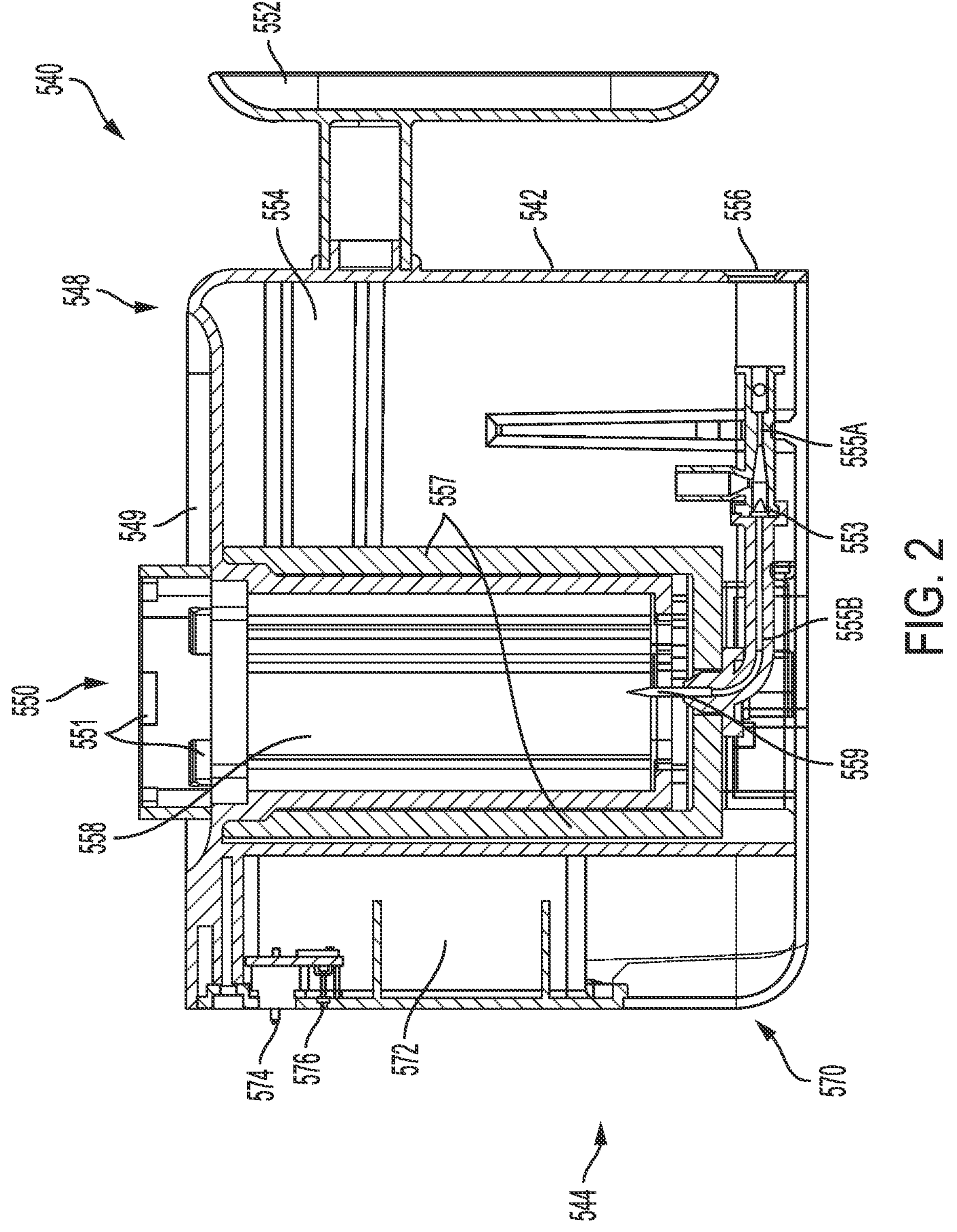
FIG. 2 is a cross-sectional view of the vial sled of FIG. 1 according to one or more embodiments shown and described herein, the cross-section along line 2-2 of FIG. 1.

In embodiments, and referring to FIG. 2, a flow sensor of the delivery device 500 may be positioned in-line with the tubing set of the delivery device 500, and in particular the multi-port needle 559, the manifolds 555A, 555B, and/or one or more of the ports 556, and may be configured to measure an amount of fluid (e.g., suspension liquid after the therapeutic particles have effectively mixed with the fluid medium) that passes thereby. Referring back to FIG. 1, the vial engagement mechanism 520 comprises a pair of lever arms 522 extending outwardly from a neck 524 of the vial engagement mechanism 520, with the neck 524 extending laterally outward from the base 512 of the console assembly 510. The neck 524 of the vial engagement mechanism 520 is disposed within a protective cover 525 such that only the pair of lever arms 522 of the vial engagement mechanism 520 extends through the protective cover 525. The protective cover 525 is operable to shield one or more internal components of the console assembly 510 from an exterior of the console assembly 510, and in particular from the vial containment region 518.

The pair of lever arms 522 is simultaneously movable with the neck 524 of the vial engagement mechanism 520 in response to an actuation of the handle 528 of the console assembly 510. Further, the pair of lever arms 522 are fixed relative to one another such that a spacing formed between the pair of lever arms 522 is relatively fixed. The pair of lever arms 522 of the vial engagement mechanism 520 is configured to securely engage the vial assembly 580 therebetween, and in particular within the spacing formed by the pair of lever arms 522. Accordingly, the vial engagement mechanism 520 is operable to securely attach the vial assembly 580 to the console assembly 510 at the vial containment region 518. Although the vial engagement mechanism 520 is shown and described herein as including a pair of lever arms 522, it should be understood that the vial engagement mechanism 520 may include various other structural configurations suitable for engaging the vial assembly 580.

Still referring to FIG. 1, the console assembly 510 further includes a safety shield 526 secured to the distal end 516 of the base 512 along the vial containment region 518. In particular, the safety shield 526 is a protective covering that is sized and shaped to enclose the vial containment region 518 of the console assembly 510 when secured thereon. The safety shield 526 is selectively attachable to the distal end 516 of the base 512 and is formed of a material that is configured to inhibit radioactive emissions from one or more radioactive doses stored within the vial containment region 518.

The distal end 516 of the console assembly 510 further includes a sled cavity 532 that is sized and shaped to receive the sled assembly 540 therein. The sled cavity 532 includes a pair of alignment features 534 extending therein, with the alignment features 534 sized and shaped to correspond with complimentary alignment features of the sled assembly 540

(e.g., alignment ribs 554) to thereby facilitate a coupling of the sled assembly 540 with the base 512 of the console assembly 510 within the sled cavity 532.

Still referring to FIG. 1, the sled assembly 540 is configured to partially receive a vial assembly 580 therein for administering therapeutic particles (e.g., radioactive fluid medium) from the delivery device 500 and to a patient. In particular, the sled assembly 540 comprises a proximal end 542 and a distal end 544 with a pair of sidewalls 546 extending therebetween. The proximal end 542 of the sled assembly 540 includes a handle 552 extending proximally therefrom. The handle 552 is configured to facilitate movement of the sled assembly 540, and in particular, an insertion of the sled assembly 540 into the sled cavity 532 of the console assembly 510. The proximal end 542 further includes one or more ports 556 for coupling one or more delivery lines (i.e., tubing) to the sled assembly 540. With the one or more delivery lines further be coupled to one or more external devices at an end of the line opposite of the ports 556, the ports 556 effectively serve to fluidly couple the sled assembly 540 to the one or more external devices via the delivery lines connected thereto. The pair of sidewalls 546 of the sled assembly 540 includes at least one alignment rib 554 extending laterally outward therefrom, where the alignment ribs 554 are sized and shaped to correspond with and mate to the pair of alignment features 534 of the console assembly 510. Accordingly, the pair of alignment ribs 554 are configured to facilitate an alignment and engagement of the sled assembly 540 with the console assembly 510 when the distal end 544 is slidably received within the sled cavity 532 of the base 512.

The sled assembly 540 further includes a top surface 548 extending from the proximal end 542 and the distal end 544 and positioned between the pair of sidewalls 546. The top surface 548 of the sled assembly includes a recessed region 549 and a locking system 550. The recessed region 549 is sized and shaped to form a recess and/or cavity along the top surface 548, where the recessed region 549 is capable of receiving and/or collecting various materials therein, including, for example, leaks of various fluid media during use of the delivery device 500. The locking system 550 of the sled assembly 540 forms an opening along the top surface 548 that is sized and shaped to receive one or more devices therein, such as a priming assembly 560 and a vial assembly 580. In some embodiments, the sled assembly 540 comes preloaded with the priming assembly 560 disposed within the locking system 550. The priming assembly 560 includes a priming line 562 extending outwardly from the locking system 550 of the sled assembly 540. The priming assembly 560 serves to purge the delivery device 500 of air prior to utilizing the delivery device 500 in a procedure.

Referring now to FIG. 2, the locking system 550 includes an annular array of projections 551 extending outwardly therefrom, and in particular, extending laterally into the aperture formed by the locking system 550 along the top surface 548. The annular array of projections 551 are formed within an inner perimeter of the locking system 550 and extend along at least two sequentially-arranged rows. The annular array of projections 551 included in the locking system 550 are configured to engage a corresponding locking feature 586 of the vial assembly 580 (See FIG. 3) to thereby securely fasten the vial assembly 580 to the sled assembly 540. It should be understood that the multiple rows of projections 551 of the locking system 550 serve to provide a double-locking system to ensure the sled assembly 540, and in particular a multi-port needle 559 of the sled assembly 540, is securely maintained through a septum 592 of the vial assembly 580 (See FIG. 3) during use of the delivery device 500 in a procedure.

The sled assembly 540 further includes a vial chamber 558 that is sized and shaped to receive the priming assembly 560 and the vial assembly 580 therein, respectively. In other words, the vial chamber 558 is sized to individually receive both the priming assembly 560 and the vial assembly 580 separate from one another. The vial chamber 558 is encapsulated around a protective chamber or shield 557 disposed about the vial chamber 558. The protective shield 557 is formed of a material configured to inhibit radioactive emissions from extending outwardly from the vial chamber 558, such as, for example, a metal. Additionally, the sled assembly 540 includes a needle extending through the protective shield 557 and into the vial chamber 558 along a bottom end of the vial chamber 558. The multi-port needle 559 is fixedly secured relative to the vial chamber 558 such that any devices received through the aperture of the locking system 550 and into the vial chamber 558 are to encounter and interact with the multi-port needle 559 (e.g., the priming assembly 560, the vial assembly 580, and the like).

Still referring to FIG. 2, the multi-port needle 559 is coupled to a distal manifold 555A and a proximal manifold 555B disposed within the sled assembly 540, and in particular the manifold 555A, 555B is positioned beneath the vial chamber 558 and the protective shield 557. The proximal manifold 555B is fluidly coupled to the multi-port needle 559 and the distal manifold 555A is fluidly coupled to the one or more ports 556 of the sled assembly 540. The proximal manifold 555B is in fluid communication with the distal manifold 555A through a one-way check valve 553 disposed therebetween.

Accordingly, the proximal manifold 555B is in fluid communication with the one or more ports 556 via the distal manifold 555A, however, the one or more ports 556 are not in fluid communication with the proximal manifold 555B due to a position of the one-way check valve 553 disposed between the manifolds 555A, 555B. Thus, the multi-port needle 559 is in fluid communication with the one or more delivery lines and/or devices coupled to the sled assembly 540 at the one or more ports 556 via the manifolds 555A, 555B secured therebetween. The one or more ports 556 of the sled assembly 540 may be coupled to a bag (e.g., saline bag), a syringe, a catheter, and/or the like via one or more delivery lines coupled thereto. In other embodiments, the multi-port needle 559 may be a cannula, catheter, or similar mechanism through which to inject and receive fluid and/or a solution as described herein.

Still referring to FIG. 2, the sled assembly 540 includes a removable battery pack 570 coupled to the sled assembly 540 along the distal end 544. The removable battery pack 570 comprises a battery 572, electrical contacts 574, and a removable tab 576. The battery 572 of the delivery device 500 is isolated from one or more fluid paths and radiation sources due to a location of the battery 572 in the removable battery pack 570.

The electrical contacts 574 of the removable battery pack 570 extend outwardly from the removable battery pack 570 and are operable to contact against and interact with corresponding electrical contacts 511 of the console assembly 510 (See FIG. 1) when the sled assembly 540 is coupled to the base 512 at the sled cavity 532. Accordingly, the removable battery pack 570 is operable to provide electrical power to the delivery device 500, and in particular the console assembly 510, when the sled assembly 540 is coupled to the console assembly 510.

Additionally, as will be described in greater detail herein, in some embodiments the locking system 550 may include at least one planar wall relative to a remaining circular orientation of the locking system 550. In this instance, an aperture formed by the locking system 550 through the top surface 548 of the sled assembly 540 is irregularly-shaped, rather than circularly-shaped as shown and described above. In this instance, the vial assembly 580 includes an locking feature 586 that has a shape and size that corresponds to the locking system 550, and in particular the at least one planar wall such that the vial assembly 580 is received within the sled assembly 540 only when an orientation of the vial assembly 580 corresponds with an alignment of the locking feature 586 and the locking system 550. In other words, a corresponding planar wall 586A of the locking feature 586 (See FIG. 3) must be aligned with the planar wall of the locking system 550 for the vial assembly 580 to be receivable within an aperture formed by the locking system 550 of the sled assembly 540.

Figure 3:
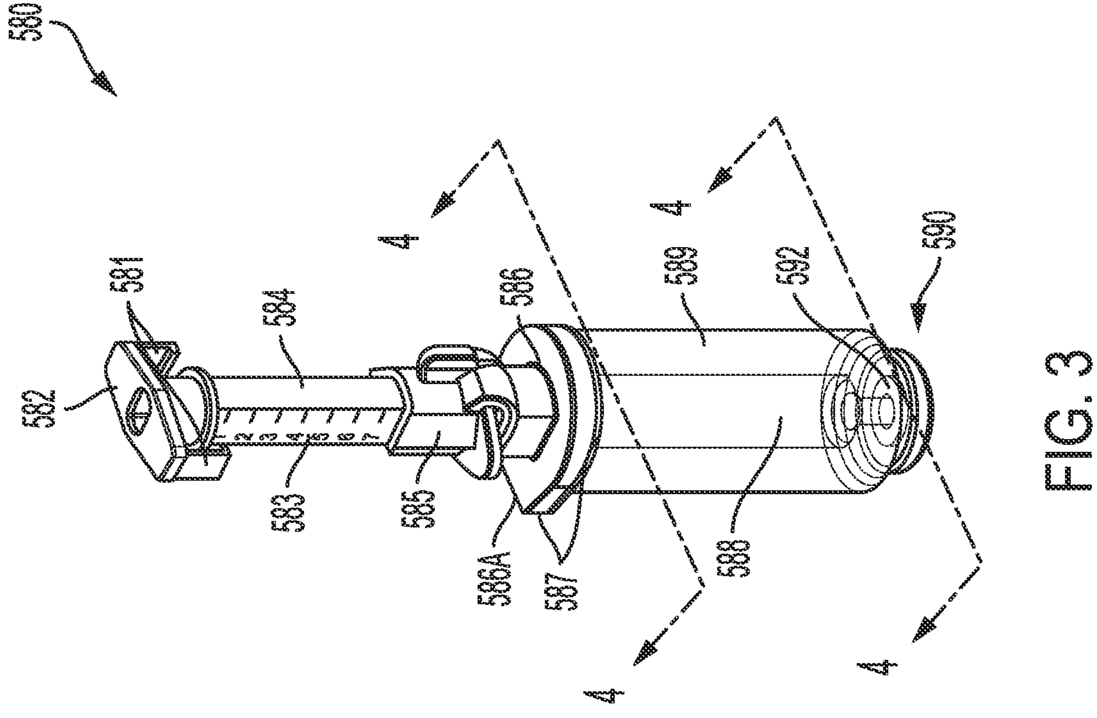
FIG. 3 is a perspective view of a vial assembly including an engagement head according to one or more embodiments shown and described herein.

Referring now to FIG. 3, the vial assembly 580 of the delivery device 500 is depicted. The vial assembly 580 comprises an engagement head 582, a plunger 584, an locking feature 586, and a vial body 589. In particular, the engagement head 582 of the vial assembly 580 is positioned at a terminal end of the plunger 584 opposite of the locking feature 586 and the vial body 589. The engagement head 582 includes a pair of arms 581 extending laterally outward relative to a longitudinal length of the plunger 584 extending downwardly therefrom. In the present example, the engagement head 582 is integrally formed with the plunger 584, however, it should be understood that in other embodiments the engagement head 582 and the plunger 584 may be separate features fastened thereto. In either instance, the engagement head 582 and the plunger 584 is movable relative to the locking feature 586 and the vial body 589 such that the engagement head 582 and the plunger 584 are slidably translatable through the locking feature 586 and the vial body 589. In particular, as will be described in greater detail herein, the plunger 584 may translate into and out of an internal chamber 588 of the vial body 589 in response to a linear translation of the vial engagement mechanism 520 when the engagement head 582 is secured to the pair of lever arms 522.

The plunger 584 includes a plurality of indicia and/or markings 583 positioned along a longitudinal length of the plunger 584. The plurality of markings 583 is indicative of a relative extension of the engagement head 582 and the plunger 584 from the locking feature 586 and the vial body 589. As briefly noted above, the engagement head 582 is configured to attach the vial assembly 580 to the vial engagement mechanism 520. In particular, the pair of arms 581 of the engagement head 582 are sized and shaped to couple with the pair of lever arms 522 of the vial engagement mechanism 520 when the vial assembly 580 is received within the sled assembly 540 and the sled assembly is inserted into the sled cavity 532 of the console assembly 510. As will be described in greater detail herein, the pair of lever arms 522 are received between the pair of arms 581 of the engagement head 582 and the plunger 584 in response to a predetermined translation force applied to the vial engagement mechanism 520. The engagement head 582 and the plunger 584 may be formed of various materials, including, but not limited to, a metal, plastic, and/or the like.

Still referring to FIG. 3, the vial assembly 580 further includes a safety tab 585 coupled to the plunger 584 relatively above the locking feature 586 and below the engagement head 582 such that the safety tab 585 is positioned along the longitudinal length of the plunger 584. The safety tab 585 may be formed of various materials, such as, for example, a plastic, and is preassembled onto the vial assembly 580 prior to a use of the delivery device 500. The safety tab 585 is removably fastened to the plunger 584 and inhibits the plunger 584 from translating relative to the vial body 589. In particular, the safety tab 585 abuts against the locking feature 586 in response to an application of linear force onto the plunger 584 to translate the plunger 584 relatively downward into the vial body 589. In this instance, the safety tab 585 is configured to inhibit an inadvertent movement of the plunger 584, and in response, an inadvertent delivery of a fluid media stored within the internal chamber 588 of the vial body 589 (e.g., therapeutic particles, radioembolizing beads). As will be described in greater detail herein, the safety tab 585 is selectively disengaged from the plunger 584 in response to a coupling of the vial assembly 580 with the vial engagement mechanism 520, and in particular an engagement of the pair of lever arms 522 with the engagement head 582.

Referring back to FIG. 3, the locking feature 586 extends about a top end of the vial body 589. In the present example, the locking feature 586 of the vial assembly 580 comprises a bushing that defines a lateral edge 587 extending laterally outward along an outer perimeter of the locking feature 586. The lateral edge 587 of the locking feature 586 is sized and shaped to engage the annular array of projections 551 of the locking system 550 when the vial assembly 580 is received within the vial chamber 558 of the sled assembly 540. As will be described in greater detail herein, the locking feature 586, and in particular the lateral edge 587 of the locking feature 586, is configured to securely fasten the vial assembly 580 to the locking system 550 to inhibit removal of the vial body 589 from the vial chamber 558 of the sled assembly 540 during use of the delivery device 500 in a procedure. In some embodiments, as briefly described above, the locking feature 586 includes at least one planar wall 586A such that the locking feature 586 comprises an irregular-profile. The at least one planar wall 586A is configured to correspond to the planar wall 550A of the locking system 550 such that an alignment of the planar walls 550A, 586A is required for the vial assembly 580 to be received through an aperture formed by the locking system 550.

Still referring to FIG. 3, the vial body 589 extends downwardly relative from the locking feature 586 and has a longitudinal length that is sized to receive at least a portion of a longitudinal length of the plunger 584 therein. By way of example only, a longitudinal length of the vial body 589 may be about 8 millimeters to about 10 millimeters, and in the present example comprises 9 millimeters, while a longitudinal length of the plunger 584 may be about 9 millimeters to about 11 millimeters, and in the present example comprises 10 millimeters. Accordingly, in some embodiments a longitudinal length of the plunger 584 exceed a longitudinal length of the vial body 589 such that a translation of the plunger 584 into the internal chamber 588 of the vial body 589 causes a fluid media stored therein to be transferred outward from the vial body 589. As will be described in greater detail herein, a translation of the plunger 584 through the internal chamber 588 of the vial body 589 provides for an administration of a fluid media stored within the vial body 589 outward from the vial assembly 580. The vial body 589 may be formed of various materials, including, for example, a thermoplastic polymer, copolyester, polycarbonate, a biocompatible plastic, polysulfone, ceramics, metals, and/or the like.

The vial body 589 is of the present example is formed of a material that is configured to inhibit radioactive emissions from a fluid media stored within the internal chamber 588 of the vial body 589. For example, the vial body 589 may be formed of a plastic, such as polycarbonate, and have a width of approximately 9 millimeters (mm). A density and material composition of the vial body 589 may collectively inhibit beta radiation emission from electron particles stored within the internal chamber 588. In the present example, a chemical composition of the plastic of the vial body 589, along with the 9 mm wall thickness, provides a plurality of atoms disposed within the vial body 589 that are capable of encountering the electron particles generating beta radiation and reducing an emission of said radiation from the vial assembly 580. Accordingly, the vial assembly 580 allows an operator to handle the radioactive material stored within the vial body 589 without being exposed to beta radiation. It should be understood that various other materials and/or wall sections may be incorporated in the vial body 589 of the vial assembly 580 in other embodiments without departing from the scope of the present disclosure.

Still referring to FIG. 3, the vial body 589 of the vial assembly 580 is sealed at a first terminal end 598 by the locking feature 586. The vial assembly 580 further includes a cap 590 positioned at an opposing, terminal end of the vial body 589 opposite of the locking feature 586, such that the cap 590 seals a second terminal end of the vial body 589 of the vial assembly 580. Additionally, the vial assembly 580 includes a septum 592 positioned adjacent to the cap 590 and in fluid communication with a terminal end of the vial body 589 opposite of the locking feature 586. The septum 592 forms a seal against a terminal end of the vial body 589 and the cap 590 retains the septum 592 therein. The septum 592 may be formed of various materials, including, for example, an elastomer, silicon, bromobutyl elastomer, rubber, urethanes, and/or the like. The septum 592 is configured to provide an air-tight seal for the vial body 589 to thereby inhibit a release of a fluid media stored therein (e.g., radioembolizing beads). As will be described in greater detail herein, the septum 592 of the vial assembly 580 is configured to be punctured by the multi-port needle 559 of the sled assembly 540 when the vial assembly 580 is received within the vial chamber 558, thereby establishing fluid communication between the vial body 589 and the sled assembly 540. In other embodiments, the septum 592 may be omitted entirely for an alternative device, such as, for example, a valve system, needle injection port, and/or the like.

Referring to FIG. 4, the vial assembly 580 further includes a stopper 594 fixedly coupled to a terminal end of the plunger 584 opposite of the engagement head 582. In this instance, with the plunger 584 coupled to, and slidably translatable through, the internal chamber 588 of the vial body 589, the stopper 594 is effectively disposed within the vial body 589. Accordingly, it should be understood that the stopper 594 is sized and shaped in accordance with a size (e.g., a diameter) of the internal chamber 588 of the vial body 589. The stopper 594 is secured to the plunger 584 such that the stopper 594 is slidably translatable through the vial body 589 in response to a translation of the plunger 584 through the vial body 589. The stopper 594 is defined by two or more ribs 593 extending laterally outward and one or more troughs 595 defined between at least two ribs 593.

The stopper 594 is configured to form a liquid-seal against the internal chamber 588 of the vial body 589, and is formed of a various polymers with a predetermined viscoelasticity. For example, in some embodiments the stopper 594 is formed of an elastomer, silicone, rubber, urethane, plastic, polyethylene, polypropylene, and/or the like. In this instance, the stopper 594 is operable to inhibit a fluid media stored within the vial body 589 from extending (i.e., leaking) past the stopper 594 and out of the vial body 589. In particular, the two or more ribs 593 of the stopper 594 abut against, and form a seal along, the internal chamber 588 of the vial body 589 to thereby inhibit a fluid media from passing beyond the ribs 593. The one or more troughs 595 formed between the two or more ribs 593 of the stopper 594 are configured to receive, and more specifically capture, any fluid media that may inadvertently extend (i.e., leak) beyond the ribs 593 of the stopper 594. Accordingly, the one or more troughs 595 serve as a safety mechanism of the vial assembly 580 to ensure a fluid media is maintained within the vial body 589 and not exposed beyond the vial assembly 580.

Still referring to FIG. 4, the two or more ribs 593 of the stopper 594 are additionally configured to push a fluid media stored within the vial body 589 in one or more directions therein (e.g., toward the cap 590) in response to a translation of the plunger 584. With the ribs 593 of the stopper 594 pressed against the internal chamber 588 of the vial body 589, translation of the plunger 584 provides for a translation of the ribs 593 against and along the internal chamber 588 of the vial body 589 such that any fluid media located in front (i.e., beneath) of the stopper 594 is effectively redirected within the vial body 589 in a direction of travel of the plunger 584 and the stopper 594. The vial assembly 580 further includes an annular washer 596 disposed within the vial body 589. In particular, the annular washer 596 is securely fixed to the plunger 584 adjacent to the stopper 594, which is secured to the plunger 584 at a terminal end opposite of the engagement head 582. Accordingly, the annular washer 596 is secured to the plunger 584 and disposed within the vial body 589 adjacent to the stopper 594. With the annular washer 596 secured to the plunger 584 adjacent to the stopper 594, the annular washer 596 is effectively disposed within the vial body 589.

Figure 5:
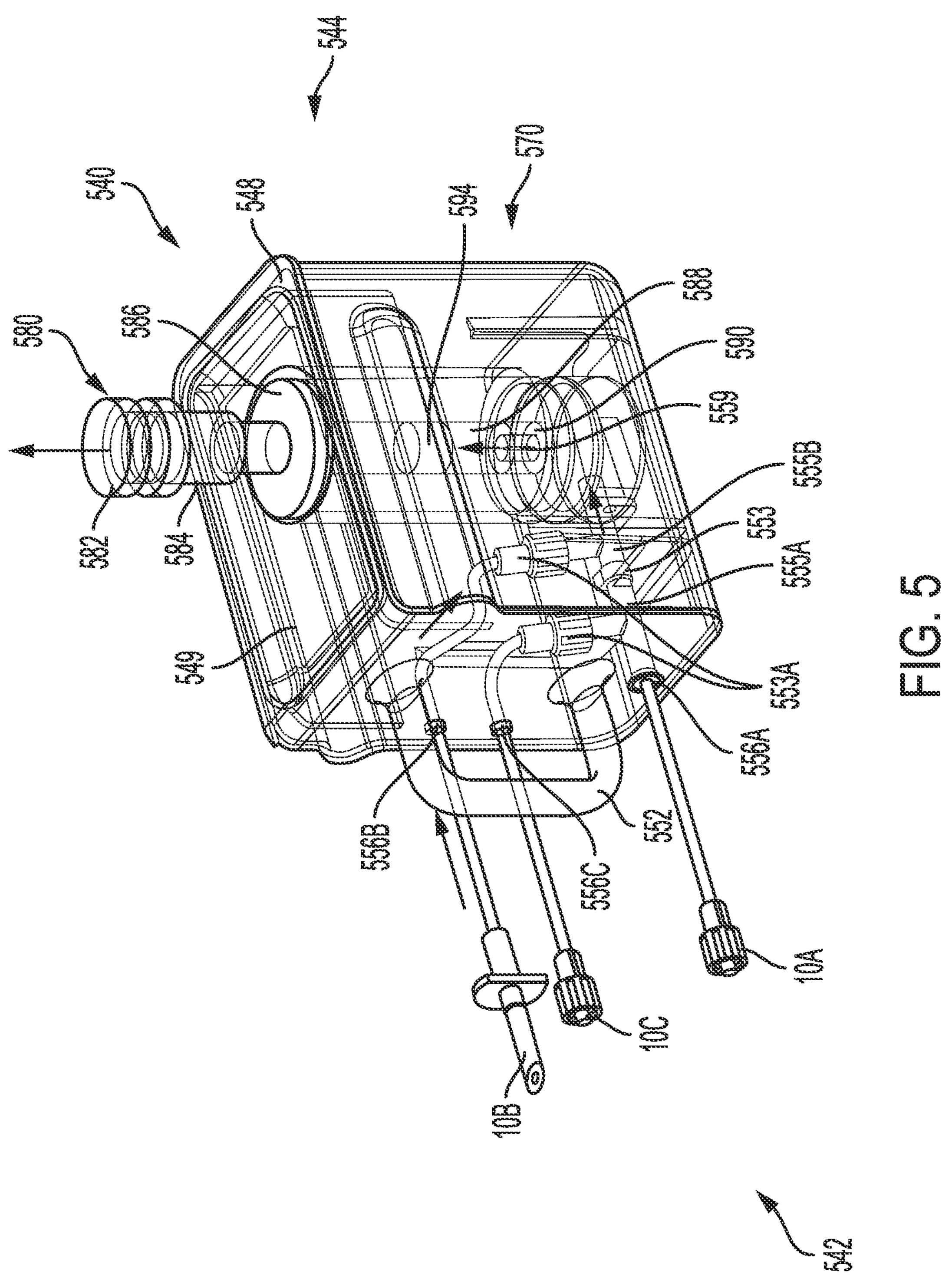
FIG. 5 is a perspective view of the vial sled of FIG. 1 with the vial assembly of FIG. 3 received therein, with a series of delivery lines coupled to the vial sled according to one or more embodiments shown and described herein.

Referring now to FIG. 5, in response to determining that the battery 572 contains or other power source provides a sufficient amount of power, one or more delivery lines are coupled to the sled assembly 540 via the one or more ports 556. In particular, a dose delivery line 10A is coupled to the sled assembly 540 at a delivery port 556A, a contrast line 10B is coupled to the sled assembly 540 at a contrast port 556B, and a flushing line 10C is coupled to the sled assembly 540 at a flushing port 556C. An opposing end of the dose delivery line 10A is initially coupled to a fluid reservoir, such as, for example, a collection bowl. As will be described in greater detail herein, the dose delivery line 10A may be subsequently coupled to an external device, such as a catheter, once the sled assembly 540 has been effectively primed by a fluid medium via the contrast line 10B. An opposing end of the flushing line 10C is coupled to an external device, such as, for example, a syringe. With both the dose delivery line 10A and the flushing line 10C coupled to the sled assembly 540, the sled assembly 540 is flushed with a fluid medium (e.g., saline) from the syringe coupled to the flushing line 10C. In this instance, the fluid medium is injected through the flushing line 10C, into the distal manifold 555A of the sled assembly 540, and out of the sled assembly 540 through the dose delivery line 10A. Accordingly, the fluid medium is ultimately received at the collection bowl and disposed thereat by the dose delivery line 10A.

With the distal manifold 555A of the sled assembly 540 separated from the proximal manifold 555B by the one-way valve 553 disposed therebetween, the fluid medium flushed through the distal manifold 555A from the syringe (via the flushing port 556C) is prevented from passing through the proximal manifold 555B and the multi-port needle 559 coupled thereto. Rather, the fluid medium injected from the syringe and through the flushing line 10C is received at the flushing port 556C, passed through the distal manifold 555A in fluid communication with the flushing port 556C, and redirected by the one-way valve 553 towards the dose delivery port 556A that is coupled to the dose delivery line 10A. In this instance, the dose delivery line 10A receives and transfers the fluid medium to the collection bowl coupled thereto, such that the fluid medium is not directed beyond the one-way valve 553 and into the proximal manifold 555B that is in fluid communication with the multi-port needle 559.

The contrast line 10B is coupled to the sled assembly 540 at a contrast port 556B. An opposing end of the contrast line 10B is coupled to a fluid medium supply, such as, for example, a bag secured to the console assembly 510 via the attachment device 538. In the present example, the bag is a saline bag such that the fluid medium stored therein is saline. In this instance, with the sled assembly 540 including the priming assembly 560 positioned within the vial chamber 558 and the needle end 568 in fluid communication with the multi-port needle 559, a syringe is fluidly coupled to the priming line 562 of the priming assembly 560 and a plunger of the syringe is drawn back to pull saline through the contrast line 10B, the contrast port 556B, the sled assembly 540, the priming line 562 and into the syringe from the saline bag. The plunger of the syringe is thereafter pushed inwards to transfer the extracted saline back through the priming line 562, the central body 564, the elongated shaft 566, and the needle end of the priming assembly 560 such that the saline is received into the multi-port needle 559 of the sled assembly 540. Accordingly, the manifolds 555A, 555B of the sled assembly 540 are effectively primed with the saline from the syringe as the multi-port needle 559 that received the saline from the priming assembly 560 is in fluid communication with the manifolds 555A, 555B. With the manifolds 555A, 555B in further fluid communication with the dose delivery line 10A via the delivery port 556A, the saline is effectively distributed to the collection bowl coupled thereto.

Referring now to FIG. 5, the sled assembly 540 is coupled to one or more external devices via the one or more ports 556. In particular, the sled assembly 540 is fluidly coupled to a catheter (e.g., microcatheter) via the dose delivery line 10A that is coupled to the delivery port 556A of the sled assembly 540. In this instance, the catheter is in fluid communication with the sled assembly 540 via the dose delivery line 10A. Further at step 718, the sled assembly 540 is fluidly coupled to a contrast source, such as, for example, a saline bag secured to the console assembly 510 via the attachment device 538 (See FIG. 1). The sled assembly 540 is in fluid communication with the saline bag via a contrast line 10B coupled to the contrast port 556B of the sled assembly 540. In this instance, the saline bag is in fluid communication with the sled assembly 540 via the contrast line 10B secured to the contrast port 556B.

The contrast port 556B is in fluid communication with the proximal manifold 555B while the delivery port 556A is in fluid communication with the distal manifold 555A. As will be described in greater detail herein, saline from the saline bag may be withdrawn through the multi-port needle 559 of the sled assembly 540 and into the vial body 589 of the vial assembly 580 as the contrast port 556B is coupled to the proximal manifold 555B, rather than the distal manifold 555A which is separated from the proximal manifold 555B by the one-way check valve 553 disposed therebetween.

Figure 6:
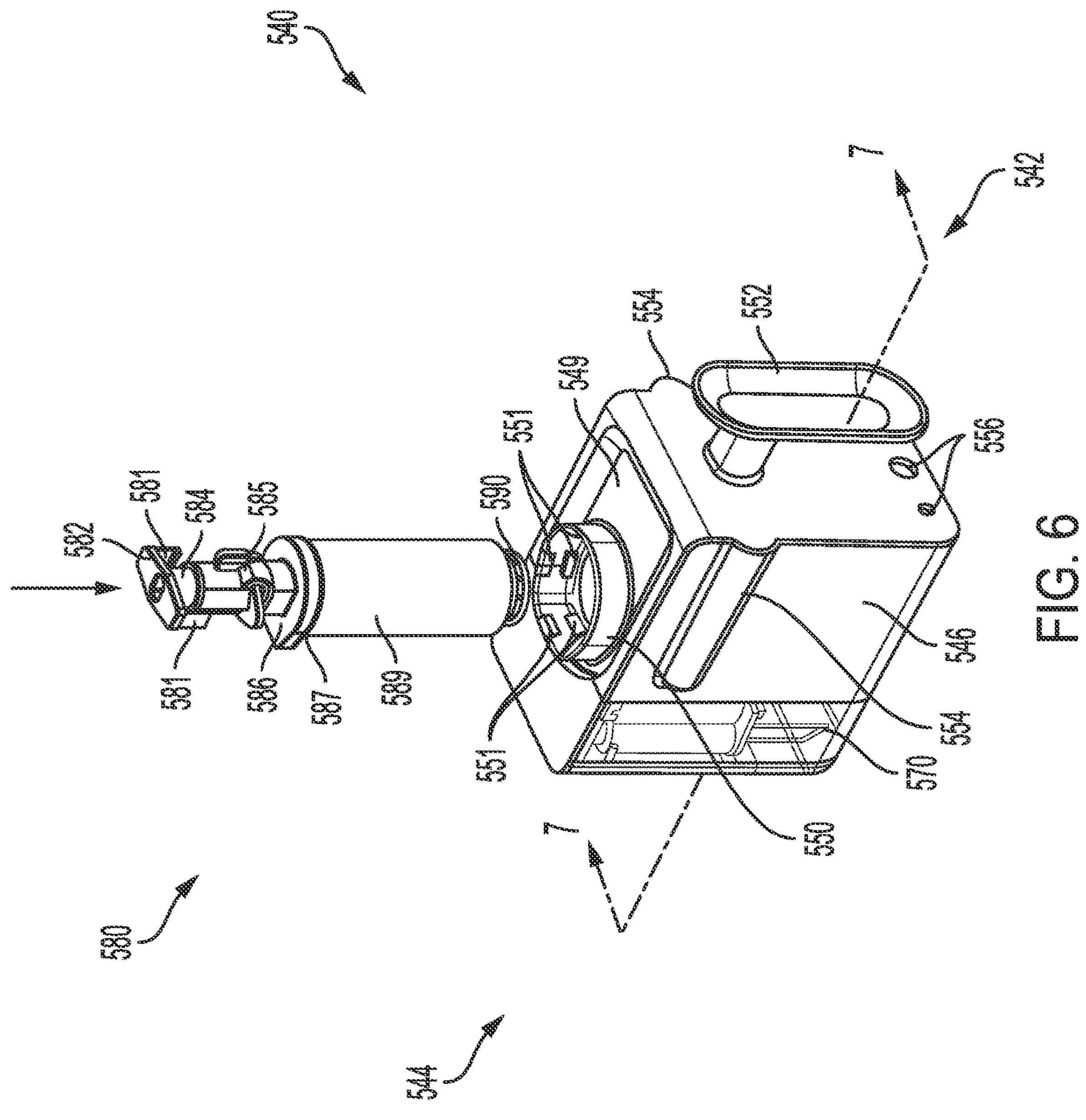
FIG. 6 is a perspective view of the vial sled of FIG. 1 with the vial assembly of FIG. 3 inserted therein according to one or more embodiments shown and described herein.

Referring now to FIG. 6, the vial assembly 580 is slidably inserted into the sled assembly 540. The cap 590 of the vial assembly 580 is inserted through the aperture formed by the locking system 550 at the top surface 548 of the sled assembly 540 and the vial assembly 580 is gradually inserted therethrough until the locking feature 586 contacts the locking system 550.

Figure 7B:
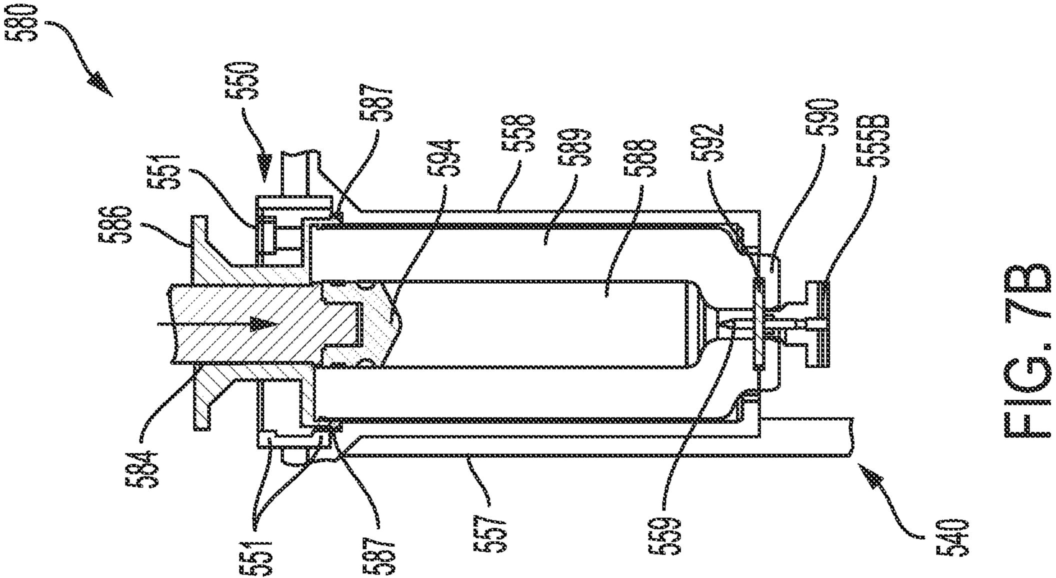
FIG. 7B is a partial cross-sectional view of the vial assembly of FIG. 3 inserted into the vial sled of FIG. 1 at a full locking position, with the cross-section taken along line 7-7 of FIG. 5.
Figure 7A:
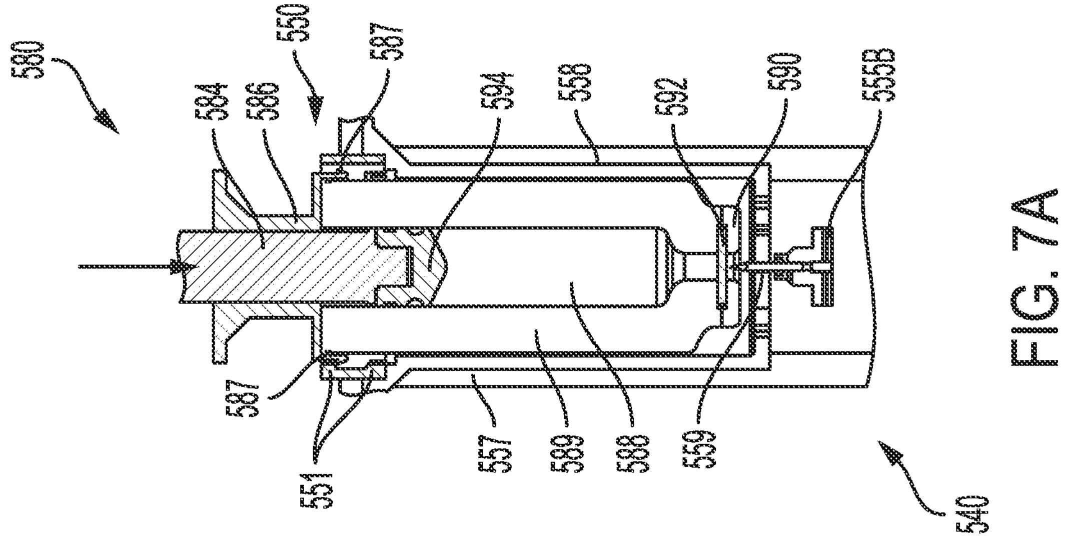
FIG. 7A is a partial cross-sectional view of the vial assembly of FIG. 3 inserted into the vial sled of FIG. 3 at an initial locking position, with the cross-section taken along line 7-7 of FIG. 6.

Referring now to FIG. 7A, the vial assembly 580 is shown disposed within the vial assembly 580, and in particular the vial body 589 is inserted within the vial chamber 558 with the cap 590 positioned proximate to the multi-port needle 559. In this instance, the lateral edge 587 of the locking feature 586 encounters a first row of the annular array of projections 551 of the locking system 550. Continued advancement of the vial assembly 580 into the sled assembly 540 causes the annular array of projections 551 positioned along the first row to flex outwardly in response to an application of force generated thereon by the lateral edge 587. In other words, the lateral edge 587 of the locking feature 586 presses outwardly against the annular array of projections 551 in response to the vial assembly 580 being received within the vial chamber 558.

As the annular array of projections 551 of the locking system 550 flex outwardly relative to the lateral edge 587 disposed therein, a continued translation of the vial assembly 580 into the vial chamber 558 causes the lateral edge 587 of the locking feature 586 to advance beyond a first row of the annular array of projections 551 such that the applied-force thereon from the lateral edge 587 is removed. In this instance, the annular array of projections 551 along the first row are permitted to flex inwardly and return to a default position with the lateral edge 587 positioned underneath the first row of projections 551. In some embodiments, a feedback is generated (e.g., an audible click) by the annular array of projections 551 when the lateral edge 587 is extended therethrough to thereby indicate to an operator that the vial assembly 580 is engaged with the locking system 550. Accordingly, with the first row of projections 551 positioned over the lateral edge 587 of the locking feature 586, the locking system 550 effectively inhibits a withdrawal of the vial assembly 580 from the vial chamber 558 of the sled assembly 540 due to an impediment formed by the first row of projections 551. In this instance, the multi-port needle 559 is positioned against and/or received through the cap 590 but is not in contact with the septum 592.

Figure 11:
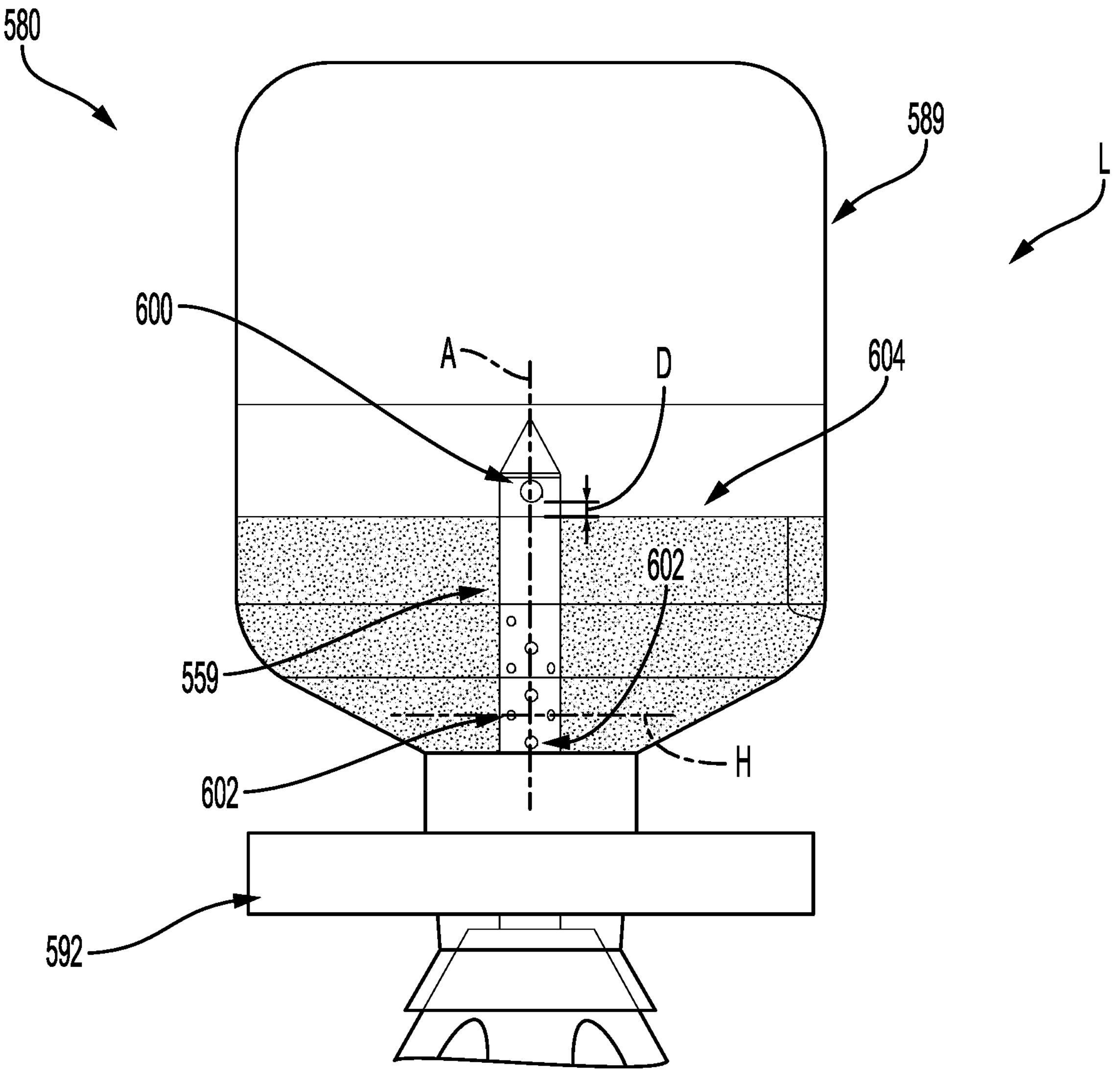
FIG. 11 is side elevation view of the vial assembly of FIG. 3 inserted into the vial sled of FIG. 1 at a full locking position with a needle coupled to a delivery line further coupled to the vial sled according to one or more embodiments shown and described herein.

Referring now to FIG. 67B, a continued translation of the vial assembly 580 into the vial chamber 558 of the sled assembly 540 provides for a subsequent engagement between the lateral edge 587 of the locking feature 586 and the locking system 550. In particular, the lateral edge 587 encounters a second row of the annular array of projections 551 of the locking system 550. Continued advancement of the vial assembly 580 into the sled assembly 540 causes the projections 551 positioned along the second row to flex outwardly in response to an application of force generated thereon by the lateral edge 587. As the lateral edge 587 advances past the projections 551, the lateral edge 587 presses outwardly against the projections 551 until the lateral edge 587 of the locking feature 586 advances beyond the second row of projections 551 to achieve a locking position L (FIG. 11).

In this instance, the applied-force from the lateral edge 587 is removed and the annular array of projections 551 along the second row are permitted to flex inwardly and return to a default position with the lateral edge 587 positioned underneath the second row of projections 551. Accordingly, with the second row of projections 551 positioned over the lateral edge 587 of the locking feature 586, the locking system 550 effectively inhibits a withdrawal of the vial assembly 580 from the vial chamber 558 of the sled assembly 540 due to an impediment formed by the second row of projections 551. In this instance in the locking position L, the multi-port needle 559 is positioned against and received through the cap 590 and the septum 592. More particularly, the multi-port needle 559 punctures the septum 592 of the vial assembly 580 such that the sled assembly 540 is in fluid communication with the vial body 589 of the vial assembly 580 through the multi-port needle 559.

Figure 8:
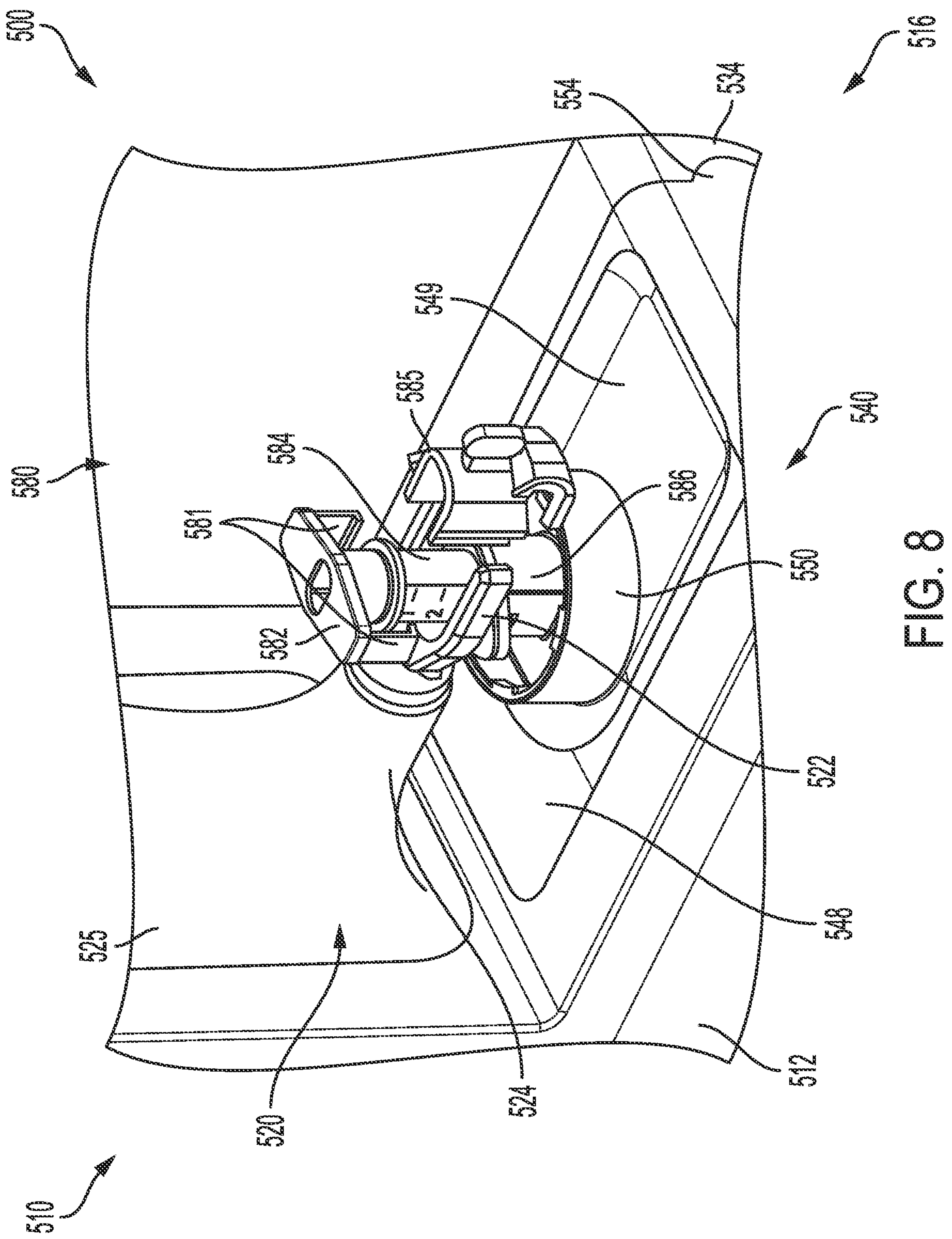
FIG. 8 is a partial-perspective view of the vial sled coupled to the delivery device of FIG. 1 with the lever arm coupled to the vial assembly of FIG. 3 according to one or more embodiments shown and described herein.

Referring now to FIGS. 1 and 8, with the vial assembly 580 securely coupled to the sled assembly 540, the sled assembly 540 is coupled to the console assembly 510 by translating the proximal end 542 of the sled assembly 540 toward and into the distal end 516 of the console assembly 510. In particular, the proximal end 542 of the sled assembly 540 is directed into the sled cavity 532 of the console assembly 510 by aligning the alignment ribs 554 of the sled assembly 540 with the alignment features 534 of the console assembly 510. Once the distal end 544 and the proximal end 542 of the sled assembly 540 are fully seated within the sled cavity 532 of the console assembly 510, the electrical contacts 574 (FIG. 2) of the removable battery pack 570 interact with corresponding electrical contacts 511 (FIG. 1) of the console assembly 510. In this instance, power from the battery 572 is transmitted to the console assembly 510 via the electrical contacts 574, thereby activating the console assembly 510 of the delivery device 500. In this instance, the interface display 530 of the console assembly 510 is activated to display pertinent, real-time information relating to the delivery device 500 during a procedure.

Referring back to FIG. 8, with the distal end 544 of the sled assembly 540 fully seated within the sled cavity 532 and the vial engagement mechanism 520 translated to a lower position, the pair of lever arms 522 engage the safety tab 585 of the vial assembly 580 thereby decoupling the safety tab 585 from the plunger 584. In other words, as the sled assembly 540 is translated into the sled cavity 532 in response to a force applied along the handle 552 at the proximal end 542, a position of the lever arms 522 of the vial engagement mechanism 520 are aligned with and encounter the safety tab 585 of the vial assembly 580. Accordingly, a continued translation of the sled assembly 540 into the sled cavity 532 provides for a disengagement of the safety tab 585 from the plunger 584 by the pair of lever arms 522. In this instance, the plunger 584 of the vial assembly 580 is uninhibited from translating into and/or out of the internal chamber 588 of the vial body 589 in response to an actuation of the vial engagement mechanism 520 coupled thereto.

Figure 9:
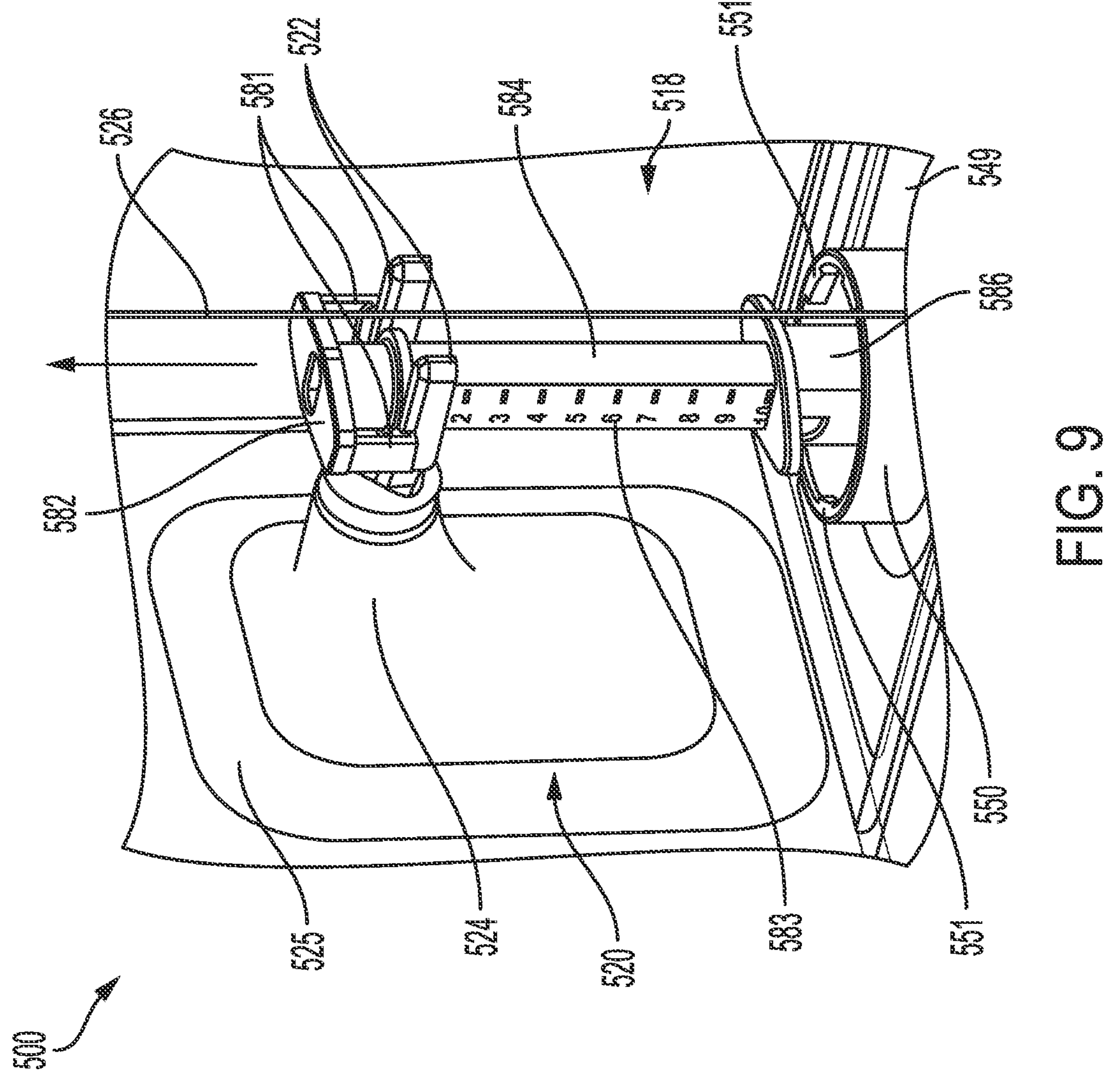
FIG. 9 is a perspective view of the vial sled coupled to the delivery device of FIG. 1, with the lever arm coupled to the vial assembly of FIG. 3 and translated to an extended position according to one or more embodiments shown and described herein.

Referring now to FIG. 9, the handle 528 of the console assembly 510 is actuated (e.g., translated relative downward) to thereby move (e.g., linearly translate) the vial engagement mechanism 520 within the vial containment region 518 distally away from the sled cavity 532 and the sled assembly 540 received therein. In this instance, with the pair of lever arms 522 of the vial engagement mechanism 520 positioned about the plunger 584 of the vial assembly 580, translation of the neck 524 and the pair of lever arms 522 causes the pair of lever arms 522 to engage the engagement head 582, and in particular a bottom end of the pair of arms 581. With a removal of the safety tab 585, the plunger 584 is operable to translate upward and out of the vial body 589 of the vial assembly 580 in response to a translation of the vial engagement mechanism 520. Accordingly, the plunger 584 translates upward simultaneous with the translation of the vial engagement mechanism 520, due to the pair of arms 581 of the engagement head 582 being pulled upwardly by the pair of lever arms 522, in response to an actuation of the handle 528.

In this instance, the pair of lever arms 522 of the vial engagement mechanism 520 is not securely coupled to the pair of arms 581 of the engagement head 582. Rather, the pair of lever arms 522 are merely positioned beneath the pair of arms 581 such that translation of the neck 524 of the vial engagement mechanism 520 causes the pair of lever arms 522 to abut against and pull the pair of arms 581 upward. It should be understood that the annular array of projections 551 of the locking system 550 inhibits a movement and/or an upward translation of the vial assembly 580, and in particular the vial body 589, from the vial chamber 558 of the sled assembly 540 as the vial engagement mechanism 520 pulls the plunger 584 of the vial assembly 580 relatively upward within the vial containment region 518. Additionally, it should further be understood that the alignment features 534 of the console assembly 510 inhibit a movement and/or upward translation of the sled assembly 540 from the sled cavity 532 of the console assembly 510 as the vial engagement mechanism 520 pulls the vial assembly 580 stored within the sled assembly 540 relatively upward within the vial containment region 518.

Still referring to FIG. 9, continued actuation of the handle 528 of the console assembly 510 provides for a continued translation of the vial engagement mechanism 520, and the plunger 584 as a result, until the annular washer 596 encounters the locking feature 586 (See FIG. 4). In this instance, the annular washer 596 inhibits the plunger 584 from translating further relative to the vial body 589 despite a continued actuation of the handle 528 of the console assembly 510. With the annular washer 596 of the vial assembly 580 abutting against the locking feature 586 and thereby inhibiting the plunger 584 from further translating out of the internal chamber 588 of the vial body 589 (and the aperture formed by the locking system 550), continued actuation of the handle 528 causes the pair of arms 581 of the engagement head 582 to flex outwardly relative to the plunger 584 due to an upward force applied thereto by the pair of lever arms 522 in response to the vial engagement mechanism 520 translating upward and the plunger 584 being inhibited from moving further.

In other words, with the pair of lever arms 522 pressed against the pair of arms 581 of the engagement head 582, continued translation of the neck 524 of the vial engagement mechanism 520 causes the pair of lever arms 522 to translate upward thereby applying a force against the pair of arms 581 of the engagement head 582. With the engagement head 582 integrally formed with the plunger 584 and the plunger 584 inhibited from translating further relative to the vial body 589 due to an impediment formed between the annular washer 596 and the locking feature 586, the pair of arms 581 of the engagement head 582 are flexibly deformed to expand outwardly to accommodate an upward translation of the pair of lever arms 522. As a result, the pair of lever arms 522 of the vial engagement mechanism 520 are securely coupled to the pair of arms 581 of the engagement head 582 via a snap-fit engagement, thereby locking the vial engagement mechanism 520 to the vial assembly 580.

Referring again to FIG. 5, as the vial engagement mechanism 520 and the plunger 584 are simultaneously translated within the vial containment region 518, a negative pressure is generated within the internal chamber 588 of the vial body 589 due to a retraction of the stopper 594. In this instance, with the saline bag coupled to the sled assembly 540 via the contrast line 10B and the contrast port 556B, saline from the saline bag is pulled into the internal chamber 588 of the vial body 589 through the proximal manifold 555B and the multi-port needle 559. Accordingly, with the vial body 589 being preloaded with a radioactive fluid media (e.g., radioembolizing microspheres), the saline is effectively mixed with the radioactive fluid media within the vial body 589 as the plunger 584 is retracted from the internal chamber 588 and the negative pressure is generated through the delivery device 500.

Figure 10:
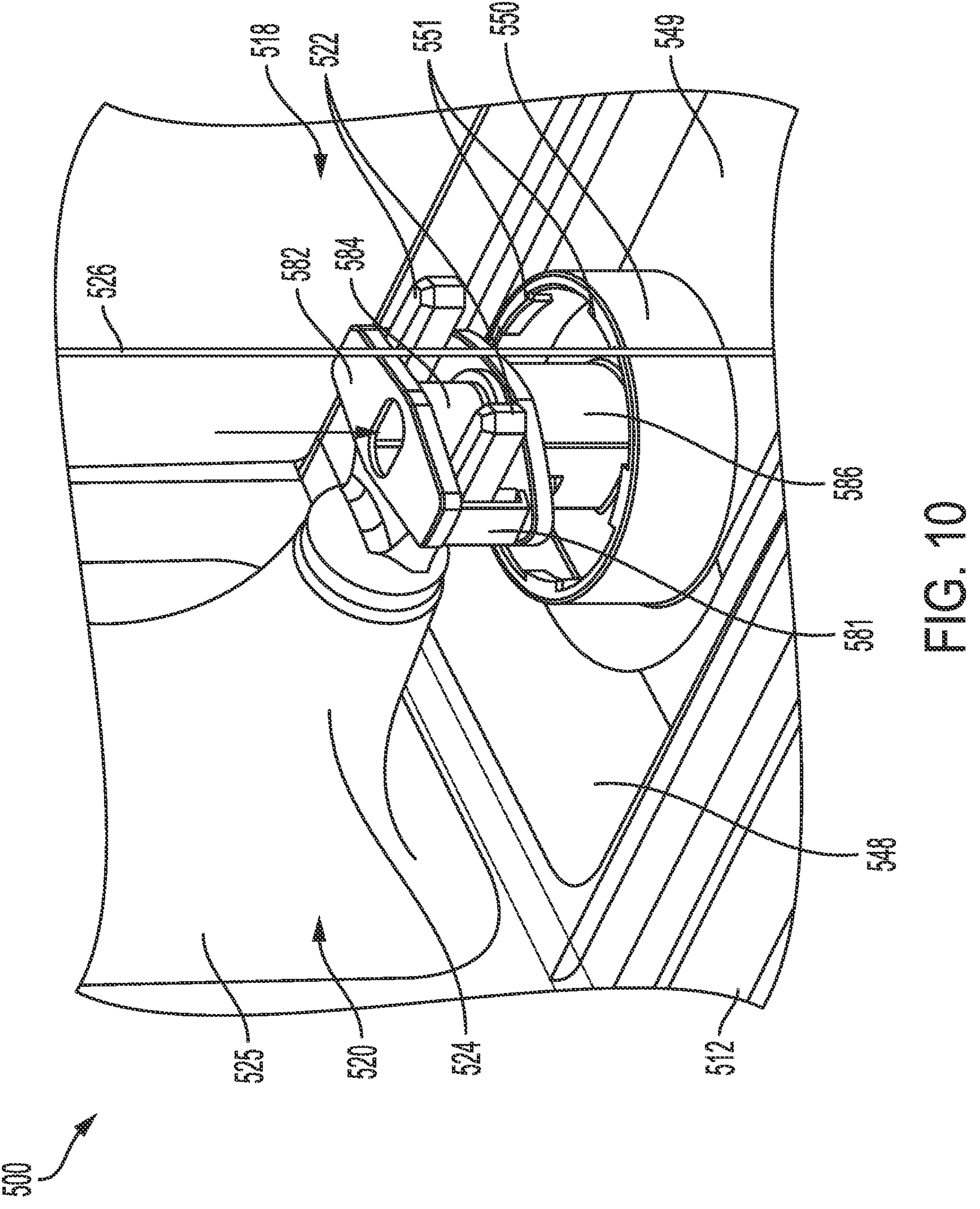
FIG. 10 is a perspective view of the vial sled coupled to the delivery device of FIG. 1, with the lever arm coupled to the vial assembly of FIG. 3 and translated to a lowered position according to one or more embodiments shown and described herein.

Referring now to FIG. 10, actuation of the handle 528 in an opposite direction (e.g., translated and/or pivoted downward relative to the base 512) provides for a simultaneous movement (e.g., linear translation) of the vial engagement mechanism 520. In this instance, the neck 524 translates downward toward the sled cavity 532 thereby causing the plunger 584 to translate into the vial body 589 due to a secured engagement between the pair of arms 581 of the engagement head 582 and the pair of lever arms 522 of the vial engagement mechanism 520. With the stopper 594 movably disposed within the vial body 589, translation of the plunger 584 causes a simultaneous translation of the stopper 594 through the vial body 589 thereby generating a positive pressure therein. As a result, a dose of the saline and radioactive fluid media mixture stored within the internal chamber 588 is transferred outward of the vial body 589 through the multi-port needle 559 and into the proximal manifold 555B. With the one-way check valve 553 configured to permit fluid communication from the proximal manifold 555B to the distal manifold 555A, the dose is delivered therethrough and into the dose delivery line 10A via the dose delivery port 556A.

Referring back to FIG. 5, the sled assembly 540 further includes one-way check valves 553A in-line with the contrast line 10B and the flushing line 10C. In particular, the one-way check valves 553A are configured to permit fluid communication from the contrast port 556B and the flushing port 556C into the manifolds 555A, 555B, and further configured to prevent fluid communication from the manifolds 555A, 555B to the contrast port 556B and the flushing port 556C. Accordingly, it should be understood that the dose delivered from the vial body 589 to the manifold 555A, 555B is incapable of being directed into the contrast line 10B or the flushing line 10C due to the one-way check valves 553A positioned therein. Thus, the dose is directed to the dose delivery port 556A and received at the catheter fluidly coupled thereto by the dose delivery line 10A. In other words, the one-way check valves 553A prevent a backflow of fluid into the sled assembly 540 and/or the vial assembly 580 coupled thereto.

II. Multi-Port Needle Embodiments

As briefly noted above, in embodiments described herein the delivery device 500 includes a multi-port needle 559, as described in greater detail below with respect to FIGS. 11-14. Referring to FIG. 11, multi-port needle 559 is configured to be injected through a septum 592 into the vial assembly 580 to move to a locked position L. In an embodiment, the multi-port needle 559 when injected into the vial assembly 580 pre-mixing includes at least a top distal port 600 of a first diameter 606 (FIGS. 12A and 12B) that is disposed at a position above a top of the settled particulate 604 (e.g., the radioactive microspheres that may be used for radioembolization, or chemoembolization microspheres used for chemoembolization). The multi-port needle 559 further includes at least one bottom proximal port 602 of a second diameter 608 (FIGS. 12A and 12B) disposed between a distal end and a proximal end of the multi-port needle 599 proximal to the top distal port 600. The at least one bottom proximal port 602 includes a second diameter 608 that is smaller than the first diameter 606. Further, the at least one bottom proximal port 602 is configured to create a high velocity fluid jet stream for mixing when acting as an outlet for fluid drawn in for injection into the vial assembly 580.

Referring to FIG. 11, eight (8) bottom proximal ports 602 are evenly spaced about a circumference of the multi-port needle 559 at positions that are 45 degrees apart. The proximal ports 602 are spaced and sized to optimize fluid output velocity. After the fluid is mixed with the particulate material 604, the mixed solution may be drawn from the vial assembly 580 in through the multi-port needle 559 via the ports 600, 602 back into the syringe. A connected lever, such as the handle 528 coupled to the vial engagement mechanism 520, may assist with injection of fluid into the vial assembly 580 through the ports 600, 602 or receive the mixed solution back through the ports 600, 602 for delivery in a procedure.

In embodiments, the particulate material delivery assembly includes the delivery device 500. The delivery device 500 includes, as described herein, the console assembly 510 including a console with a vial containment region 518, the vial assembly 580, the vial engagement mechanism 520, and the multi-port needle 559. The vial assembly 580 includes the particulate material 604. The vial engagement mechanism 520 extends from the console within the vial containment region 518. The vial engagement mechanism 520 is configured to engage the vial assembly 580 and move the vial to the locked position L of FIG. 11. The multi-port needle 559 is configured to puncture the septum 592 of the vial assembly 580 when the vial assembly 580 is in the locked position L.

The multi-port needle 559 of FIG. 11 includes the top distal port 600 of the first diameter 606 and the plurality of bottom proximal ports 602, each of the second diameter 608 that is smaller than the first diameter 606. The top distal port 600 is further configured to be at a distance D above and spaced away from the particulate material 604 in the vial assembly 580 when in the locked position L. During delivery, spheres as the particulate material 604 may be fully suspended as described in greater detail herein. However, if there is a delay in delivery, the spheres may settle out. The dual port feature of the multi-port needle 559 with the top distal port 600 at the distance D above the particulate material 604 in the locked position L and spaced from the proximal ports 602 is configured to permit the proximal ports 602 to clog during settling while the top distal port 602 remains open to permit fluid delivery. A user may then resuspend the spheres by activating the handle. The top distal port 600 and each bottom proximal port 602 is configured to inject a fluid into the vial assembly 580 to mix with the particulate material 604 upon actuation of the vial engagement mechanism 520 in a first direction (e.g., upwards) and to receive a resulting mixed fluid from the vial assembly 580 upon actuation of the vial engagement mechanism 520 in a second direction opposite the first direction (e.g., downwards).

The top distal port 600 and each bottom proximal port 602 may be configured to inject the fluid into the vial assembly to mix with the particulate material 604 upon actuation of the vial engagement mechanism 520 in the first direction that is a negative pressure inducing direction and to receive the resulting mixed fluid from the vial assembly 580 upon actuation of the vial engagement mechanism 604 in the second direction that is a positive pressure inducing direction opposite the negative pressure inducing direction. Actuation of the vial engagement mechanism 520 in the negative pressure inducing direction may include an upward movement of a lever of the vial engagement mechanism 520, such as the pair of lever arms 522 coupled to the vial engagement mechanism 520 and the handle 528, with the vial assembly 580 in the locked position L. Actuation of the vial engagement mechanism 520 in the positive pressure inducing direction comprises a downward movement of the lever of the vial engagement mechanism 520 with the vial assembly 580 in the locked position L.

The top distal port 600 and the at least the bottom proximal port 602 is configured to inject the fluid into the vial assembly to mix with the particulate material upon a mix rotation of the multi-port needle and to receive the resulting mixed fluid from the vial assembly upon a delivery rotation of the multi-port needle. The mix rotation may be in a first rotation direction and the delivery rotation in the first rotation direction or in a second rotation direction opposite the first rotation direction. As non-limiting examples, the top distal port 600 and each bottom proximal port 602 may be configured to inject the fluid into the vial assembly 580 to mix with the particulate material 604 upon a corresponding rotation of the multi-port needle 559. The top distal port 600 and each bottom proximal port 602 may be configured to receive the resulting mixed fluid from the vial assembly 580 upon the corresponding rotation of the multi-port needle 559. Alternatively, top distal port 600 and each bottom proximal port 602 may be configured receive the resulting mixed fluid from the vial assembly 580 upon a corresponding rotation of the multi-port needle 559 in a second rotation direction opposite the first rotation direction.

In embodiments, the delivery device 500 is a radioembolization delivery device, the particulate material 604 is a plurality of radioembolization beads, the fluid is a saline solution, and the resulting mixed fluid (e.g., the mixed fluid solution) is a radioembolization beads-saline solution. The multi-port needle 559 may be configured to deliver the radioembolization beads-saline solution as the mixed fluid solution through the radioembolization delivery device, such as upon actuation of the vial engagement mechanism 520 in the positive pressure direction. In some embodiments, the fluid is a contrast-saline solution including a contrast agent, and the resulting mixed fluid (e.g., the mixed fluid solution) is a radioembolization beads-contrast-saline solution. The multi-port needle 559 may be configured to deliver the radioembolization beads-contrast-saline solution as the mixed fluid solution through the radioembolization delivery device. In some embodiments, the delivery device 500 is a chemoembolization delivery device, the particulate material 604 is a plurality of chemoembolization beads, and the mixed fluid solution is a beads-saline solution or a beads-contrast-saline solution.

Figure 12A:
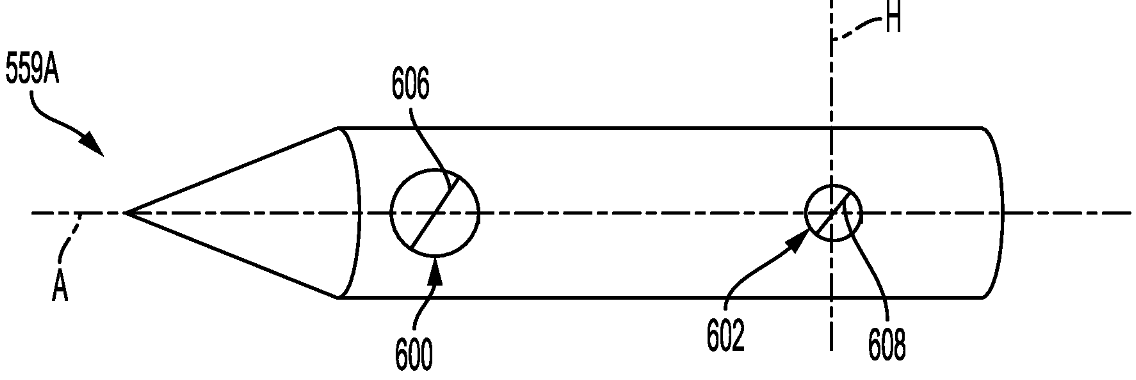
FIG. 12A is perspective view of a needle including a single top distal port.

Referring to FIG. 12A, a multi-port needle 559A is shown including a top distal port 602 having a diameter 606 and a bottom proximal port 602 having a diameter 608. The top distal port 602 includes the first diameter 606, and the bottom proximal port 604 includes the second diameter 608 that is smaller than the first diameter 606.

Figure 12B:
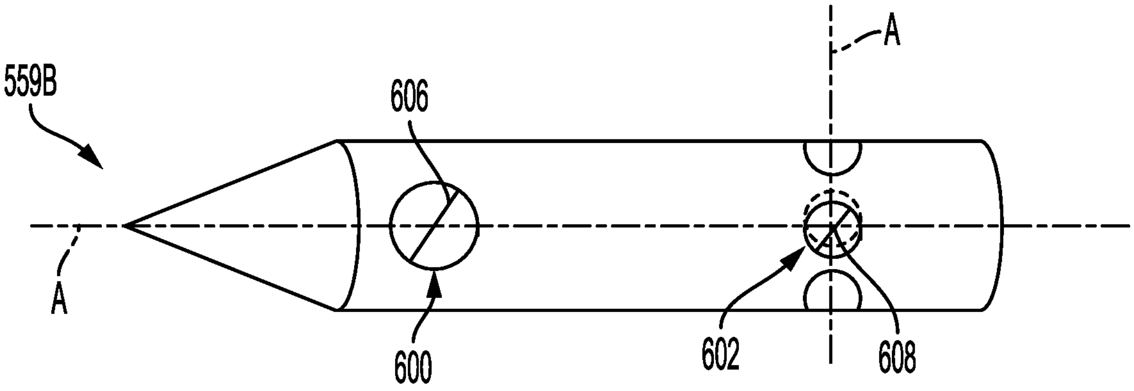
FIG. 12B is a perspective view of an embodiment of a needle including a single top distal port and four bottom proximal ports according to one or more embodiments shown and described herein.

Referring to FIG. 12B, a multi-port needle 559B is shown including the top distal port 602 and four bottom proximal ports 604. The top distal port 602 includes the first diameter 606, and each bottom proximal port 604 includes the second diameter 608 that is smaller than the first diameter 606.

Referring to both FIGS. 11 and 12B, the at least the bottom proximal port 602 of the multi-port needle 559 includes a plurality of proximal ports 602 on the multi-port needle 559. The multi-port needle 559 may include a horizontal plane H and a longitudinal axis A, the horizontal plane H perpendicular to the longitudinal axis A. The plurality of proximal ports 602 may be evenly and concentrically spaced around the multi-port needle such that the plurality of proximal ports 602 are intersected by the horizontal plane H of the multi-port needle. In an embodiment, the plurality of proximal ports 602 may be concentrically spaced around the multi-port needle such that at least two proximal ports 602 are staggered in spacing with respect to the horizontal plane H of the multi-port needle 559. The plurality of proximal ports 602 may include eight proximal ports 602, and each proximal port 602 is evenly spaced at forty-five degree positions from another proximal port 602. Alternatively the plurality of proximal ports 602 may include four proximal ports 602, and each proximal port 602 is evenly spaced at ninety degree positions from another proximal port 602. In embodiments, each proximal port 602 may be spaced at a range of from about twenty degrees to about ninety degrees from another proximal port 602. In some embodiments, a plurality of proximal ports 602 may be disposed in one or more rows on the multi-port needle 559.

Figure 13:
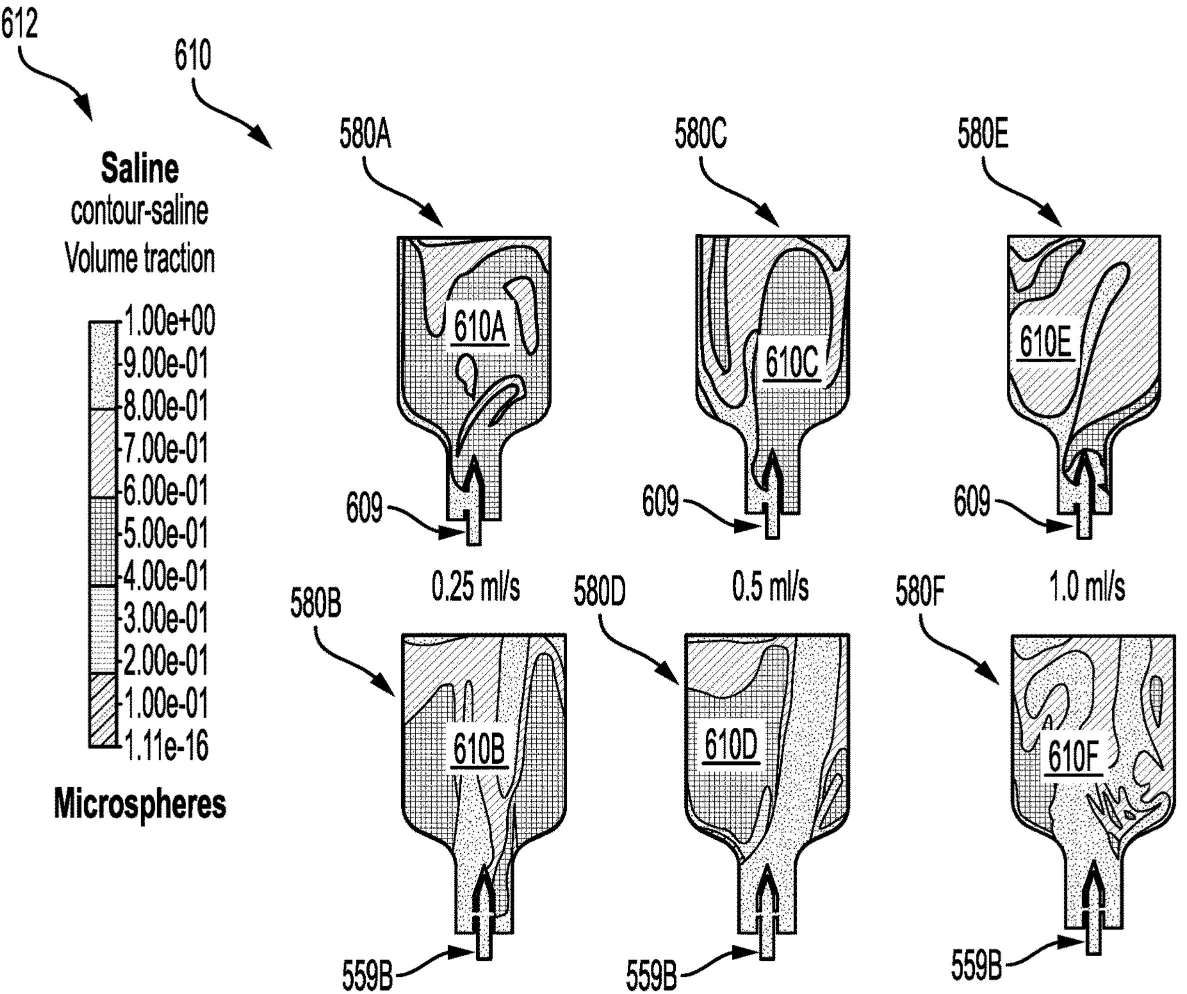
FIG. 13 is an illustration of an example of mixing test results of the needles of FIG. 12B compared to a single-port needle.

Referring to FIG. 13, an example is shown of mixing test results 610 of the multi-port needle 559B of FIG. 12B compared to a single port needle 609 at different mixing speeds. A legend 612 shows a ratio of saline to microspheres, with a level toward the saline label indicate a more homogenous mixed solution and a level toward the microspheres label indicating a more heterogeneous mixed solution in which, for example, particulate material 604 has settled toward a bottom of the vial assembly 580 due to gravity.

The vial assembly 580A and the vial assembly 580A are both mixed at a mixing speed of 0.25 ml/s. The vial assembly 580A uses the single port needle 609, and the vial assembly 580B uses the multi-port needle 559B. The flow from the single port 609 toward a left sidewall of the vial assembly 580A is shown through an angled line dividing a higher saline ratio suspension from a lower saline ratio suspension, the angled line indicative of the path of flow from the single port 609. The mixing test result 610A of the vial assembly 580A indicates the most heterogeneous mixed solution as defined by the legend 612 in comparison to the mixing test results 610B-610B using the multi-port needle 559B and/or a faster mixing speed. The mixing test results 610B for the vial assembly 580B using the multi-port needle 559B shows an improvement and more homogenous mixed solution over the mixing test results 610A.

The vial assembly 580C and the vial assembly 580D are both mixed at a mixing speed of 0.5 ml/s. The vial assembly 580C uses the single port needle 609, and the vial assembly 580D uses the multi-port needle 559B. The mixing test result 610C of the vial assembly 580C indicates a more heterogeneous mixed solution as defined by the legend 612 in comparison to the mixing test results 610D using the multi-port needle 559B. Thus, the mixing test results 610D for the vial assembly 580D using the multi-port needle 559B shows an improvement and more homogenous mixed solution over the mixing test results 610C.

The vial assembly 580E and the vial assembly 580F are both mixed at a mixing speed of 1.0 ml/s. The vial assembly 580E uses the single port needle 609, and the vial assembly 580F uses the multi-port needle 559B. The mixing test result 610E of the vial assembly 580E indicates a more heterogeneous mixed solution as defined by the legend 612 in comparison to the mixing test results 610F using the multi-port needle 559B. Thus, the mixing test results 610F for the vial assembly 580F using the multi-port needle 559B shows an improvement and more homogenous mixed solution over the mixing test results 610E.

Figure 14:
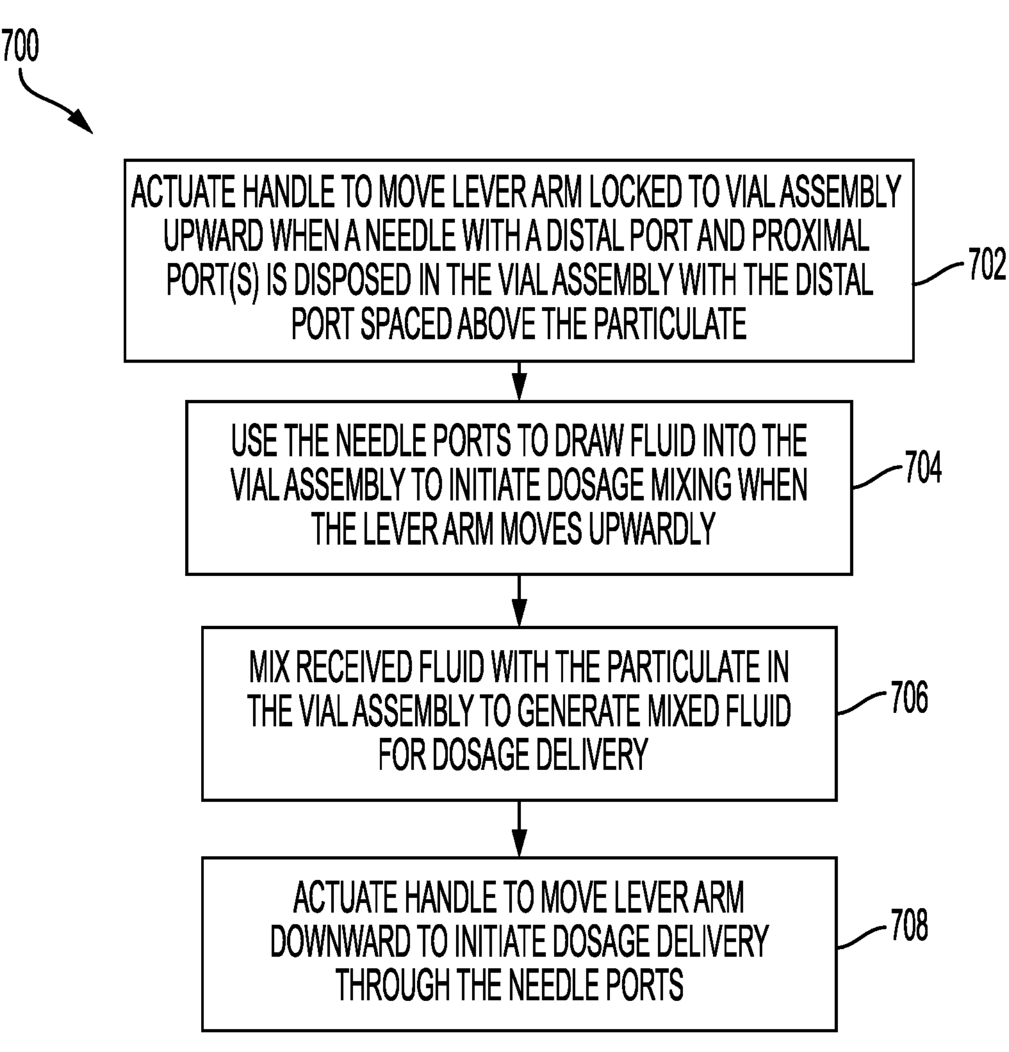
FIG. 14 is a flow diagram of an exemplary method of delivering a radioactive dose with the delivery device of FIG. 1 and multi-port needles of FIGS. 11 and 12B.

Referring to FIG. 14, a process 700 of a method of use of a particulate material delivery assembly such as the delivery device 500 to deliver particulate, such as the particulate material 604, is illustrated. The process 700 includes engaging a vial engagement mechanism 520 extending from a console of the console assembly 510 within a vial containment region 518 of the console with a vial assembly 580, the vial assembly 580 comprising the particulate material 604. The vial assembly 580 engaged with the vial engagement mechanism 520 is moved to a locked position L as described herein. A septum 592 of the vial assembly 580 is punctured with a multi-port needle 559 when the vial assembly 580 is in the locked position L. As described herein, the multi-port needle 559 includes a top distal port 600 of a first diameter 606 and at least a bottom proximal port 602 of a second diameter 608 that is smaller than the first diameter 606. The top distal port 600 is further configured to be at a distance D above and spaced away from the particulate material 604 in the vial assembly 580 when in the locked position L.

In block 702, the vial engagement mechanism 520 is actuated in a first direction. In an embodiment, the handle 528 is actuated to move a lever arm 522 locked to the vial assembly 580 upwardly when the multi-port needle 559 with the distal port 600 and proximal port(s) 602 is disposed in the vial assembly 580 with the distal port 602 spaced above the particulate material 604.

In block 704, upon such actuation of the vial engagement mechanism in the first direction, a fluid is injected through the top distal port 600 and the at least the bottom proximal port 602 into the vial assembly 580 to mix with the particulate material 604 to generate a resulting mixed fluid in the vial assembly 580. In block 706, the received fluid is mixed with the particulate material 604 in the vial assembly 580 to generate the resulting mixed fluid for dosage delivery. In an embodiment, the fluid is injected through the top distal port 600 and the at least the bottom proximal port 602 into the vial assembly 580 to mix with the particulate material 604 upon actuation of the vial engagement mechanism 520 in the first direction as a negative pressure inducing direction. Additionally or alternatively, the fluid may be injected through the top distal port 600 and the at least the bottom proximal port 602 into the vial assembly 580 to mix with the particulate material 604 upon a mix rotation of the multi-port needle 559.

In block 708, the resulting mixed fluid is received through top distal port 600 and the at least the bottom proximal port 602 from the vial assembly 580 into the multi-port needle 559 upon actuation of the vial engagement mechanism 520 in a second direction opposite the first direction. In an embodiment, the handle 528 is actuated to move a lever arm 522 locked to the vial assembly 580 downwardly to initiate dosage delivery through the ports 600, 602 of the multi-port needle 599. In an embodiment, the resulting mixed fluid is received through top distal port 600 and the at least the bottom proximal port 600 from the vial assembly 580 into the multi-port needle 559 upon actuation of the vial engagement mechanism in the second direction comprising a positive pressure inducing direction opposite the negative pressure inducing direction. Additionally or alternatively, the resulting mixed fluid may be received through top distal port 600 and the at least the bottom proximal port 600 from the vial assembly 580 into the multi-port needle 559 upon a delivery rotation of the multi-port needle 559. The delivery rotation may be a same rotation direction or a different rotation direction of the mix rotation.

The process 700 may further include delivering the resulting mixed fluid from the multi-port needle 559 through the delivery device 500 as a radioembolization delivery device of the particulate material delivery assembly. As describe herein, the particulate material 604 may include a plurality of radioembolization beads, the fluid may be a saline solution, and the resulting mixed fluid may be a radioembolization beads-saline solution.

In embodiments described herein, the multi-port needle 559 includes anti-clogging features via the at least ports 600, 602 to prevent or reduce such potential clogging while being configured to optimize mixing. The ports 600, 602 of the multi-port needle 599 cooperate to create a high velocity fluid jet stream, with the top distal port 600 as a slightly larger port that is configured to be disposed above a settled particulate material 604 in the vial assembly 580 when injected into the vial the vial assembly 580. As described herein, a ratio of the area of the ports 600, 602 to the needle inner lumen of the multi-port needle 599 and rest of the fluid path may assist to determine the number and spacing of the lower ports 602 to optimize velocity output. To optimize output velocity range, an area of a port 602, 604 may be based on an inner needle diameter cross sectional area ratio.

By way of example, and not as a limitation, such optimal flow/mixing to optimize velocity output may be achieved when a total area of all ports 600, 602 is 100% of an inner diameter of a cross-sectional area of the multi-port needle 599, which creates a higher output velocity and more optimal mixing than when the total area is above 100% of the inner diameter of the cross-sectional area of the multi-port needle 599. In embodiments, a number of ports 600, 602 may be determined by balancing mixing all areas of the bottom of a syringe housing the multi-port needle 599 with a column strength of the multi-port needle 559. Further, two rows of small bottom proximal ports 602 may be used to preserve needle column strength. The bottom proximal ports 602 may be disposed as one or more rows with respect to the horizontal plane H. A radial orientation of the ports 600, 602 may be spaced evenly to aid even mixing and optimize a resulting homogenous mixing solution.

III. Aspects Listing

Aspect 1. A particulate material delivery assembly comprises a console including a vial containment region, a vial assembly comprising a particulate material, a vial engagement mechanism extending from the console within the vial containment region, wherein the vial engagement mechanism is configured to engage the vial assembly and move the vial assembly to a locked position, and a multi-port needle configured to puncture a septum of the vial assembly when the vial assembly is in the locked position. The multi-port needle comprises a top distal port of a first diameter and at least a bottom proximal port of a second diameter that is smaller than the first diameter, the top distal port and the at least the bottom proximal port configured to inject a fluid into the vial assembly to mix with the particulate material upon actuation of the vial engagement mechanism in a first direction and to receive a resulting mixed fluid from the vial assembly upon actuation of the vial engagement mechanism in a second direction opposite the first direction. The top distal port is further configured to be at a distance above and spaced away from the particulate material in the vial assembly when in the locked position.

Aspect 2. The particulate material delivery assembly of Aspect 1, wherein the particulate material delivery assembly comprises a radioembolization delivery device, the particulate material comprises a plurality of radioembolization beads, the fluid comprises a contrast-saline solution, the resulting mixed fluid comprises a radioembolization beads-contrast-saline solution, and the multi-port needle is configured to deliver the radioembolization beads-contrast-saline solution through the radioembolization delivery device.

Aspect 3. The particulate material delivery assembly of Aspect 1 or Aspect 2, wherein the top distal port and the at least the bottom proximal port is configured to inject the fluid into the vial assembly to mix with the particulate material upon actuation of the vial engagement mechanism in the first direction comprising a negative pressure inducing direction and to receive the resulting mixed fluid from the vial assembly upon actuation of the vial engagement mechanism in the second direction comprising a positive pressure inducing direction opposite the negative pressure inducing direction.

Aspect 4. The particulate material delivery assembly of Aspect 3, wherein actuation of the vial engagement mechanism in the negative pressure inducing direction comprises an upward movement of a lever of the vial engagement mechanism with the vial assembly in the locked position, and actuation of the vial engagement mechanism in the positive pressure inducing direction comprises a downward movement of the lever of the vial engagement mechanism with the vial assembly in the locked position.

Aspect 5. The particulate material delivery assembly of Aspect 3 or Aspect 4, wherein the particulate material delivery assembly comprises a radioembolization delivery device, the particulate material comprises a plurality of radioembolization beads, the fluid comprises a saline solution, the resulting mixed fluid comprises a radioembolization beads-saline solution, and the multi-port needle is configured to deliver the radioembolization beads-saline solution through the radioembolization delivery device upon actuation of the vial engagement mechanism in the positive pressure direction.

Aspect 6. The particulate material delivery assembly of any of Aspect 3 to Aspect 5, wherein the top distal port and the at least the bottom proximal port is configured to inject the fluid into the vial assembly to mix with the particulate material upon a corresponding rotation of the multi-port needle and to receive the resulting mixed fluid from the vial assembly upon the corresponding rotation of the multi-port needle.

Aspect 7. The particulate material delivery assembly of any of Aspect 3 to Aspect 6, wherein the top distal port and the at least the bottom proximal port is configured to inject the fluid into the vial assembly to mix with the particulate material upon a corresponding rotation of the multi-port needle in a first rotation direction and to receive the resulting mixed fluid from the vial assembly upon a corresponding rotation of the multi-port needle in a second rotation direction opposite the first rotation direction.

Aspect 8. The particulate material delivery assembly of any of Aspect 1 to Aspect 7, wherein the top distal port and the at least the bottom proximal port is configured to inject the fluid into the vial assembly to mix with the particulate material upon a mix rotation of the multi-port needle and to receive the resulting mixed fluid from the vial assembly upon a delivery rotation of the multi-port needle.

Aspect 9. The particulate material delivery assembly of Aspect 8, wherein the mix rotation is in a first rotation direction and the delivery rotation is in the first rotation direction.

Aspect 10. The particulate material delivery assembly of Aspect 8, wherein the mix rotation is in a first rotation direction and the delivery rotation is in a second rotation direction opposite the first rotation direction.

Aspect 11. The particulate material delivery assembly of any of Aspect 1 to Aspect 10, wherein the at least the bottom proximal port of the multi-port needle comprises a plurality of proximal ports on the multi-port needle.

Aspect 12. The particulate material delivery assembly of Aspect 11, wherein the multi-port needle comprises a horizontal plane and a longitudinal axis, the horizontal plane perpendicular to the longitudinal axis, and the plurality of proximal ports are evenly and concentrically spaced around the multi-port needle such that the plurality of proximal ports are intersected by the horizontal plane of the multi-port needle.

Aspect 13. The particulate material delivery assembly of Aspect 11 or Aspect 12, wherein the multi-port needle comprises a horizontal plane and a longitudinal axis, the horizontal plane perpendicular to the longitudinal axis, and the plurality of proximal ports are concentrically spaced around the multi-port needle such that at least two proximal ports are staggered in spacing with respect to the horizontal plane of the multi-port needle.

Aspect 14. The particulate material delivery assembly of any of Aspect 11 to Aspect 13, wherein the plurality of proximal ports comprises eight proximal ports, and each proximal port is spaced at a range of from about twenty degrees to about ninety degrees from another proximal port.

Aspect 15. The particulate material delivery assembly of Aspect 11 to Aspect 13, wherein the plurality of proximal ports comprises four proximal ports, and each proximal port is spaced at a range of from about twenty degrees to about ninety degrees from another proximal port.

Aspect 16. A method of use of a particulate material delivery assembly to deliver particulate, comprising engaging a vial engagement mechanism extending from a console within a vial containment region of the console with a vial assembly comprising a particulate material, moving the vial assembly engaged with the vial engagement mechanism to a locked position, and puncturing a septum of the vial assembly with a multi-port needle when the vial assembly is in the locked position. The multi-port needle comprises a top distal port of a first diameter and at least a bottom proximal port of a second diameter that is smaller than the first diameter, and the top distal port is further configured to be at a distance above and spaced away from the particulate material in the vial assembly when in the locked position. The method further comprising injecting through the top distal port and the at least the bottom proximal port a fluid into the vial assembly to mix with the particulate material to generate a resulting mixed fluid in the vial assembly upon actuation of the vial engagement mechanism in a first direction, and receiving through top distal port and the at least the bottom proximal port the resulting mixed fluid from the vial assembly into the multi-port needle upon actuation of the vial engagement mechanism in a second direction opposite the first direction.

Aspect 17. The method of Aspect 16, further comprising delivering the resulting mixed fluid from the multi-port needle through a radioembolization delivery device of the particulate material delivery assembly, wherein the particulate material comprises a plurality of radioembolization beads, the fluid comprises a saline solution, and the resulting mixed fluid comprises a radioembolization beads-saline solution.

Aspect 18. The method of Aspect 16 or Aspect 17, further comprising injecting through the top distal port and the at least the bottom proximal port the fluid into the vial assembly to mix with the particulate material upon actuation of the vial engagement mechanism in the first direction comprising a negative pressure inducing direction, and receiving through top distal port and the at least the bottom proximal port the resulting mixed fluid from the vial assembly into the multi-port needle upon actuation of the vial engagement mechanism in the second direction comprising a positive pressure inducing direction opposite the negative pressure inducing direction.

Aspect 19. The method of any of Aspect 16 to Aspect 18, further comprising injecting through the top distal port and the at least the bottom proximal port the fluid into the vial assembly to mix with the particulate material upon a mix rotation of the multi-port needle, and receiving through top distal port and the at least the bottom proximal port the resulting mixed fluid from the vial assembly into the multi-port needle upon a delivery rotation of the multi-port needle, wherein the delivery rotation is one of a same rotation direction and a different rotation direction of the mix rotation.

Aspect 20. The method of any of Aspect 16 to Aspect 19, wherein the at least the bottom proximal port of the multi-port needle comprises a plurality of proximal ports on the multi-port needle.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

For the purposes of describing and defining the present disclosure it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A particulate material delivery assembly, comprising:

a console including a vial containment region;

a vial assembly comprising a particulate material;

a vial engagement mechanism extending from the console within the vial containment region, wherein the vial engagement mechanism is configured to engage the vial assembly and move the vial assembly to a locked position; and a multi-port needle configured to puncture a septum of the vial assembly when the vial assembly is in the locked position;

wherein the multi-port needle comprises a top distal port of a first diameter and at least a bottom proximal port of a second diameter that is smaller than the first diameter, wherein each of the top distal port and the at least the bottom proximal port is formed in a lateral surface of the multi-port needle, the top distal port and the at least the bottom proximal port configured to inject a fluid into the vial assembly to mix with the particulate material upon actuation of the vial engagement mechanism in a first direction and to receive a resulting mixed fluid from the vial assembly upon actuation of the vial engagement mechanism in a second direction opposite the first direction;

wherein the top distal port and the at least the bottom proximal port is configured to inject the fluid into the vial assembly to mix with the particulate material upon a mix rotation of the multi-port needle and to receive the resulting mixed fluid from the vial assembly upon a delivery rotation of the multi-port needle;

wherein the top distal port is further configured to be at a distance above and spaced away from the particulate material in the vial assembly when in the locked position.

2. The particulate material delivery assembly of claim 1, wherein the particulate material delivery assembly comprises a radioembolization delivery device, the particulate material comprises a plurality of radioembolization beads, the fluid comprises a contrast-saline solution, the resulting mixed fluid comprises a radioembolization beads-contrast-saline solution, and the multi-port needle is configured to deliver the radioembolization beads-contrast-saline solution through the radioembolization delivery device.

3. The particulate material delivery assembly of claim 1, wherein the top distal port and the at least the bottom proximal port is configured to inject the fluid into the vial assembly to mix with the particulate material upon actuation of the vial engagement mechanism in the first direction comprising a negative pressure inducing direction and to receive the resulting mixed fluid from the vial assembly upon actuation of the vial engagement mechanism in the second direction comprising a positive pressure inducing direction opposite the negative pressure inducing direction.

4. The particulate material delivery assembly of claim 3, wherein actuation of the vial engagement mechanism in the negative pressure inducing direction comprises an upward movement of a lever of the vial engagement mechanism with the vial assembly in the locked position, and actuation of the vial engagement mechanism in the positive pressure inducing direction comprises a downward movement of the lever of the vial engagement mechanism with the vial assembly in the locked position.

5. The particulate material delivery assembly of claim 3, wherein the particulate material delivery assembly comprises a radioembolization delivery device, the particulate material comprises a plurality of radioembolization beads, the fluid comprises a saline solution, the resulting mixed fluid comprises a radioembolization beads-saline solution, and the multi-port needle is configured to deliver the radioembolization beads-saline solution through the radioembolization delivery device upon actuation of the vial engagement mechanism in the positive pressure direction.

6. The particulate material delivery assembly of claim 3, wherein the top distal port and the at least the bottom proximal port is configured to inject the fluid into the vial assembly to mix with the particulate material upon a corresponding rotation of the multi-port needle as the mix rotation and to receive the resulting mixed fluid from the vial assembly upon the corresponding rotation of the multi-port needle as the delivery rotation.

7. The particulate material delivery assembly of claim 3, wherein the top distal port and the at least the bottom proximal port is configured to inject the fluid into the vial assembly to mix with the particulate material upon a corresponding rotation of the multi-port needle as the mix rotation in a first rotation direction and to receive the resulting mixed fluid from the vial assembly upon a corresponding rotation of the multi-port needle as the delivery rotation in a second rotation direction opposite the first rotation direction.

8. The particulate material delivery assembly of claim 1, wherein the mix rotation is in a first rotation direction and the delivery rotation is in the first rotation direction.

9. The particulate material delivery assembly of claim 1, wherein the mix rotation is in a first rotation direction and the delivery rotation is in a second rotation direction opposite the first rotation direction.

10. The particulate material delivery assembly of claim 1, wherein the at least the bottom proximal port of the multi-port needle comprises a plurality of proximal ports on the multi-port needle.

11. The particulate material delivery assembly of claim 10, wherein the multi-port needle comprises a horizontal plane and a longitudinal axis, the horizontal plane perpendicular to the longitudinal axis, and the plurality of proximal ports are evenly and concentrically spaced around the multi-port needle such that the plurality of proximal ports are intersected by the horizontal plane of the multi-port needle.

12. The particulate material delivery assembly of claim 10, wherein the multi-port needle comprises a horizontal plane and a longitudinal axis, the horizontal plane perpendicular to the longitudinal axis, and the plurality of proximal ports are concentrically spaced around the multi-port needle such that at least two proximal ports are staggered in spacing with respect to the horizontal plane of the multi-port needle.

13. The particulate material delivery assembly of claim 10, wherein the plurality of proximal ports comprises eight proximal ports, and each proximal port is spaced at a range of from about twenty degrees to about ninety degrees from another proximal port.

14. The particulate material delivery assembly of claim 10, wherein the plurality of proximal ports comprises four proximal ports, and each proximal port is spaced at a range of from about twenty degrees to about ninety degrees from another proximal port.

15. A method of use of a particulate material delivery assembly to deliver particulate, comprising:

engaging a vial engagement mechanism extending from a console within a vial containment region of the console with a vial assembly comprising a particulate material;

moving the vial assembly engaged with the vial engagement mechanism to a locked position;

puncturing a septum of the vial assembly with a multi-port needle when the vial assembly is in the locked position, wherein the multi-port needle comprises a top distal port of a first diameter and at least a bottom proximal port of a second diameter that is smaller than the first diameter, wherein each of the top distal port and the at least the bottom proximal port is formed in a lateral surface of the multi-port needle, and the top distal port is further configured to be at a distance above and spaced away from the particulate material in the vial assembly when in the locked position;

injecting through the top distal port and the at least the bottom proximal port a fluid into the vial assembly to mix with the particulate material to generate a resulting mixed fluid in the vial assembly upon actuation of the vial engagement mechanism in a first direction;

injecting through the top distal port and the at least the bottom proximal port the fluid into the vial assembly to mix with the particulate material upon a mix rotation of the multi-port needle;

receiving through top distal port and the at least the bottom proximal port the resulting mixed fluid from the vial assembly into the multi-port needle upon actuation of the vial engagement mechanism in a second direction opposite the first direction; and receiving through top distal port and the at least the bottom proximal port the resulting mixed fluid from the vial assembly into the multi-port needle upon a delivery rotation of the multi-port needle, wherein the delivery rotation is one of a same rotation direction and a different rotation direction of the mix rotation.

16. The method of claim 15, further comprising delivering the resulting mixed fluid from the multi-port needle through a radioembolization delivery device of the particulate material delivery assembly, wherein the particulate material comprises a plurality of radioembolization beads, the fluid comprises a saline solution, and the resulting mixed fluid comprises a radioembolization beads-saline solution.

17. The method of claim 15, further comprising injecting through the top distal port and the at least the bottom proximal port the fluid into the vial assembly to mix with the particulate material upon actuation of the vial engagement mechanism in the first direction comprising a negative pressure inducing direction; and receiving through top distal port and the at least the bottom proximal port the resulting mixed fluid from the vial assembly into the multi-port needle upon actuation of the vial engagement mechanism in the second direction comprising a positive pressure inducing direction opposite the negative pressure inducing direction.

18. The method of claim 15, wherein the at least the bottom proximal port of the multi-port needle comprises a plurality of proximal ports on the multi-port needle.

* * * * *